(12) United States Patent
Bardy

(10) Patent No.: US 8,251,946 B2
(45) Date of Patent: Aug. 28, 2012

(54) METHOD FOR CONSTRUCTING AN INSTRUMENT WITH A TWO-PART PLUNGER FOR SUBCUTANEOUS IMPLANTATION

(75) Inventor: Gust H. Bardy, Carnation, WA (US)

(73) Assignee: Cardiac Science, Inc., Bothell, WA (US)

( * ) Notice: Subject to any disclaimer, the term of this patent is extended or adjusted under 35 U.S.C. 154(b) by 61 days.

(21) Appl. No.: 12/836,512

(22) Filed: Jul. 14, 2010

(65) Prior Publication Data

US 2010/0331868 A1 Dec. 30, 2010

Related U.S. Application Data

(63) Continuation-in-part of application No. 12/815,364, filed on Jun. 14, 2010, which is a continuation of application No. 11/484,084, filed on Jul. 10, 2006, now Pat. No. 7,736,330, which is a continuation-in-part of application No. 11/345,617, filed on Feb. 1, 2006, now Pat. No. 7,780,625, which is a continuation of application No. 11/025,770, filed on Dec. 20, 2004, now abandoned, which is a continuation of application No. 10/222,719, filed on Aug. 15, 2002, now abandoned, which is a continuation of application No. 09/644,666, filed on Aug. 24, 2000, now Pat. No. 6,436,068.

(51) Int. Cl.
*A61M 31/00* (2006.01)

(52) U.S. Cl. .......................... 604/60; 604/500

(58) Field of Classification Search .............. 604/57–64, 604/117, 158, 164.01, 164.04, 164.06, 164.08, 604/274; 600/432, 567

See application file for complete search history.

(56) References Cited

U.S. PATENT DOCUMENTS

| 2,513,014 | A | | 6/1950 | Fields |
| 2,830,587 | A | | 4/1958 | Everett |
| 3,477,437 | A | * | 11/1969 | Goldberg ..................... 604/117 |
| 3,545,443 | A | | 12/1970 | Ansari |
| 4,447,223 | A | | 5/1984 | Kaye et al. |
| 4,531,938 | A | | 7/1985 | Kaye et al. |
| D295,318 | S | | 4/1988 | Gazale |
| 4,769,011 | A | | 9/1988 | Swaniger |
| D301,378 | S | | 5/1989 | Shippert |
| 4,832,687 | A | | 5/1989 | Smith, III |

(Continued)

FOREIGN PATENT DOCUMENTS

FR 2 835 436 8/2003

(Continued)

*Primary Examiner* — Christopher D Koharski
*Assistant Examiner* — Nathan R Price
(74) *Attorney, Agent, or Firm* — Patrick J. S. Inouye

(57) ABSTRACT

A method for constructing an instrument with a two-part plunger for subcutaneous implantation is provided. An incising body is formed by defining a non-circular coaxial bore and sharpening a distal bottom edge. A two-part plunger including a tongue blade assembly and a plunger assembly is constructed. The tongue blade assembly is constructed by sharpening a beveled end of a flat thin tongue blade and by affixing a straight tongue blade shaft to an end of the tongue blade opposite the beveled end. The tongue blade assembly has a length exceeding the coaxial bore. The plunger assembly is constructed by affixing a plunger to a plunger shaft on a distal end. The plunger assembly has a length exceeding the coaxial bore and is oriented adjacent to the tongue blade assembly. The two-part plunger is inserted through an end of the incising body.

15 Claims, 21 Drawing Sheets

U.S. PATENT DOCUMENTS

| | | |
|---|---|---|
| 4,900,304 A | 2/1990 | Fujioka et al. |
| 4,909,250 A | 3/1990 | Smith |
| 4,915,686 A | 4/1990 | Frederick |
| 4,936,827 A | 6/1990 | Grimm et al. |
| 4,941,874 A | 7/1990 | Sandow et al. |
| 4,950,234 A | 8/1990 | Fujioka et al. |
| 5,250,026 A | 10/1993 | Ehrlich et al. |
| 5,273,532 A | 12/1993 | Niezink et al. |
| 5,279,554 A | 1/1994 | Turley |
| 5,279,555 A | 1/1994 | Lifshey |
| 5,284,479 A | 2/1994 | De Jong |
| 5,300,106 A | 4/1994 | Dahl et al. |
| 5,304,119 A | 4/1994 | Balaban et al. |
| 5,331,966 A | 7/1994 | Bennett et al. |
| 5,358,474 A | 10/1994 | Kaldany |
| 5,405,324 A | 4/1995 | Wiegerinck |
| 5,484,403 A | 1/1996 | Yoakum et al. |
| 5,501,664 A | 3/1996 | Kaldany |
| 5,501,672 A | 3/1996 | Firth et al. |
| 5,507,807 A | 4/1996 | Shippert |
| 5,526,772 A | 6/1996 | Curkendall |
| 5,558,637 A | 9/1996 | Allonen et al. |
| 5,562,613 A | 10/1996 | Kaldany |
| 5,669,890 A | 9/1997 | Grimm |
| 5,772,671 A | 6/1998 | Harmon |
| D396,287 S | 7/1998 | Morales |
| 5,810,769 A | 9/1998 | Schlegel et al. |
| 5,827,293 A | 10/1998 | Elliot |
| 5,908,404 A | 6/1999 | Elliot |
| 5,944,732 A | 8/1999 | Raulerson et al. |
| 5,984,890 A | 11/1999 | Gast et al. |
| 6,190,350 B1 | 2/2001 | Davis et al. |
| 6,230,059 B1 | 5/2001 | Duffin |
| 6,245,052 B1 | 6/2001 | Orth et al. |
| 6,261,243 B1 | 7/2001 | Burney et al. |
| 6,293,925 B1 | 9/2001 | Safabash et al. |
| 6,317,626 B1 | 11/2001 | Warman |
| 6,488,649 B1 | 12/2002 | Lichten |
| 6,551,289 B1 | 4/2003 | Higuchi et al. |
| 6,682,480 B1 | 1/2004 | Habib et al. |
| 6,761,725 B1 | 7/2004 | Grayzel et al. |
| 7,247,160 B2 | 7/2007 | Seiler et al. |
| D593,201 S | 5/2009 | Lash et al. |
| 7,942,843 B2 | 5/2011 | Tune et al. |
| 2003/0135153 A1 | 7/2003 | Hagemeier |
| 2004/0082969 A1* | 4/2004 | Kerr ............................ 606/205 |
| 2005/0216028 A1* | 9/2005 | Hart et al. .................... 606/108 |
| 2009/0018603 A1 | 1/2009 | Mitelberg et al. |

FOREIGN PATENT DOCUMENTS

| | | |
|---|---|---|
| WO | PCT/GB99/02389 | 7/1999 |
| WO | PCT/GB99/02393 | 7/1999 |
| WO | PCT/US99/08353 | 10/1999 |

* cited by examiner

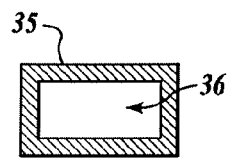
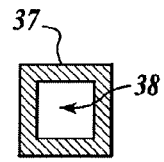
FIG.5A    FIG.5B
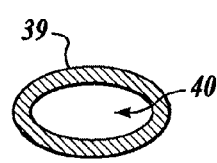
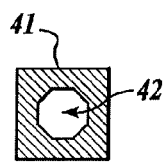
FIG.5C    FIG.5D
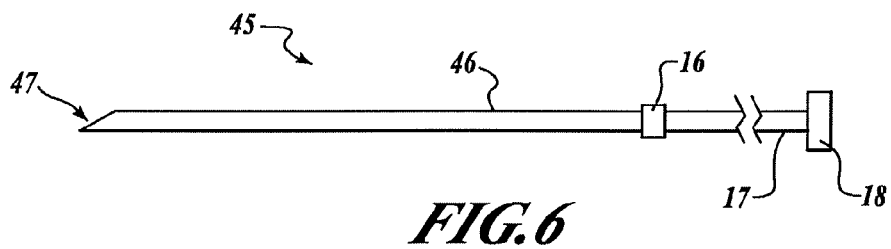
FIG.6
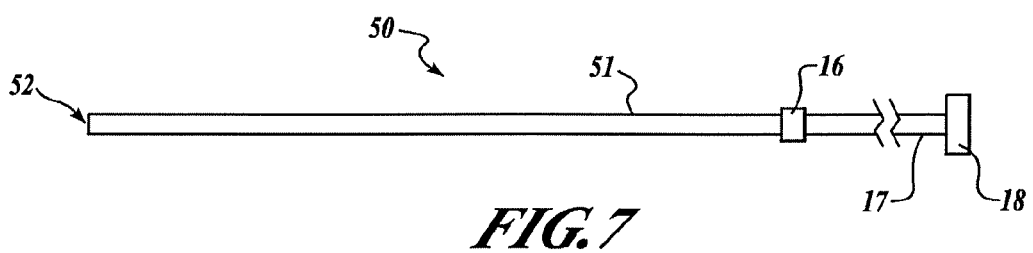
FIG.7

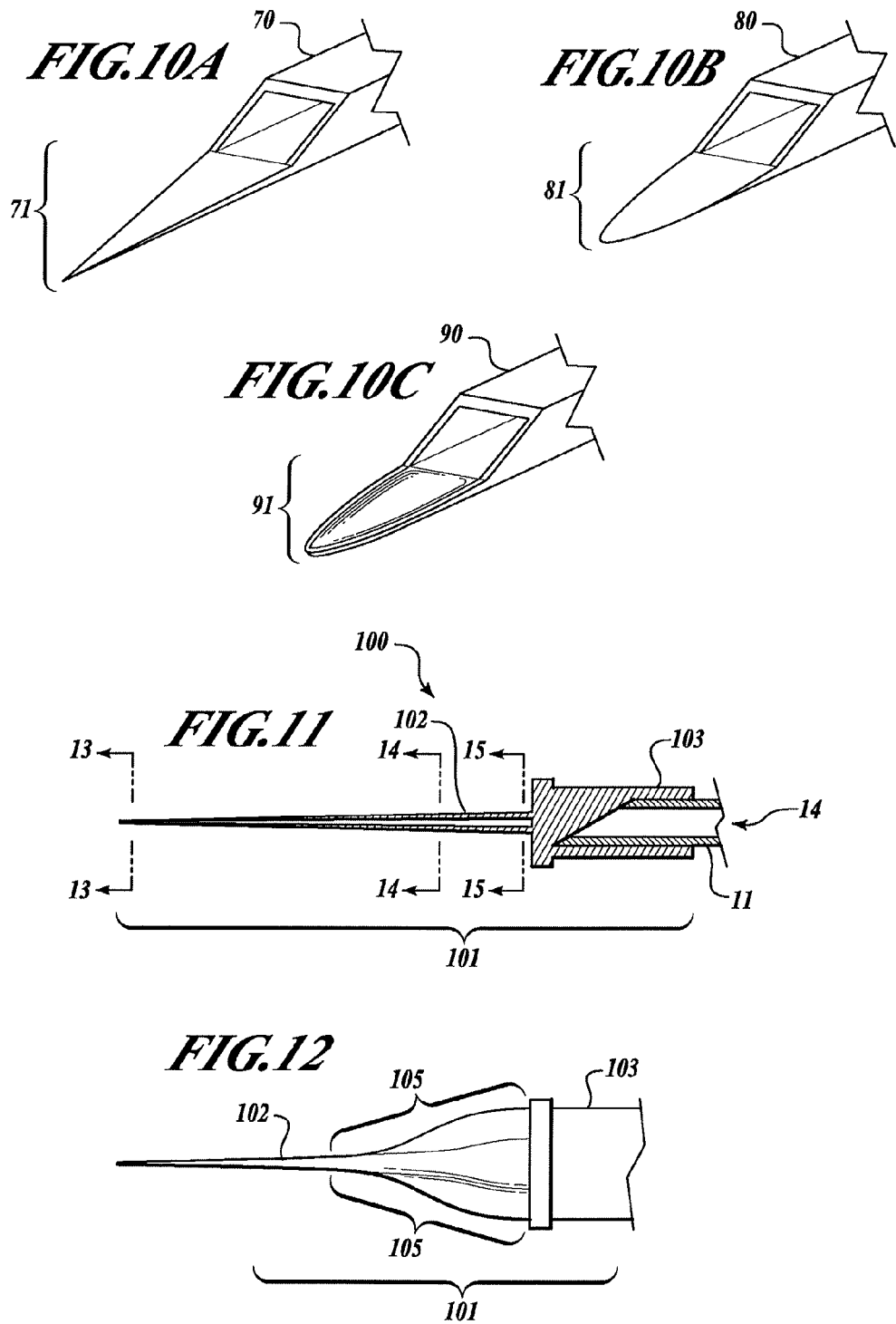

o  *FIG.13*

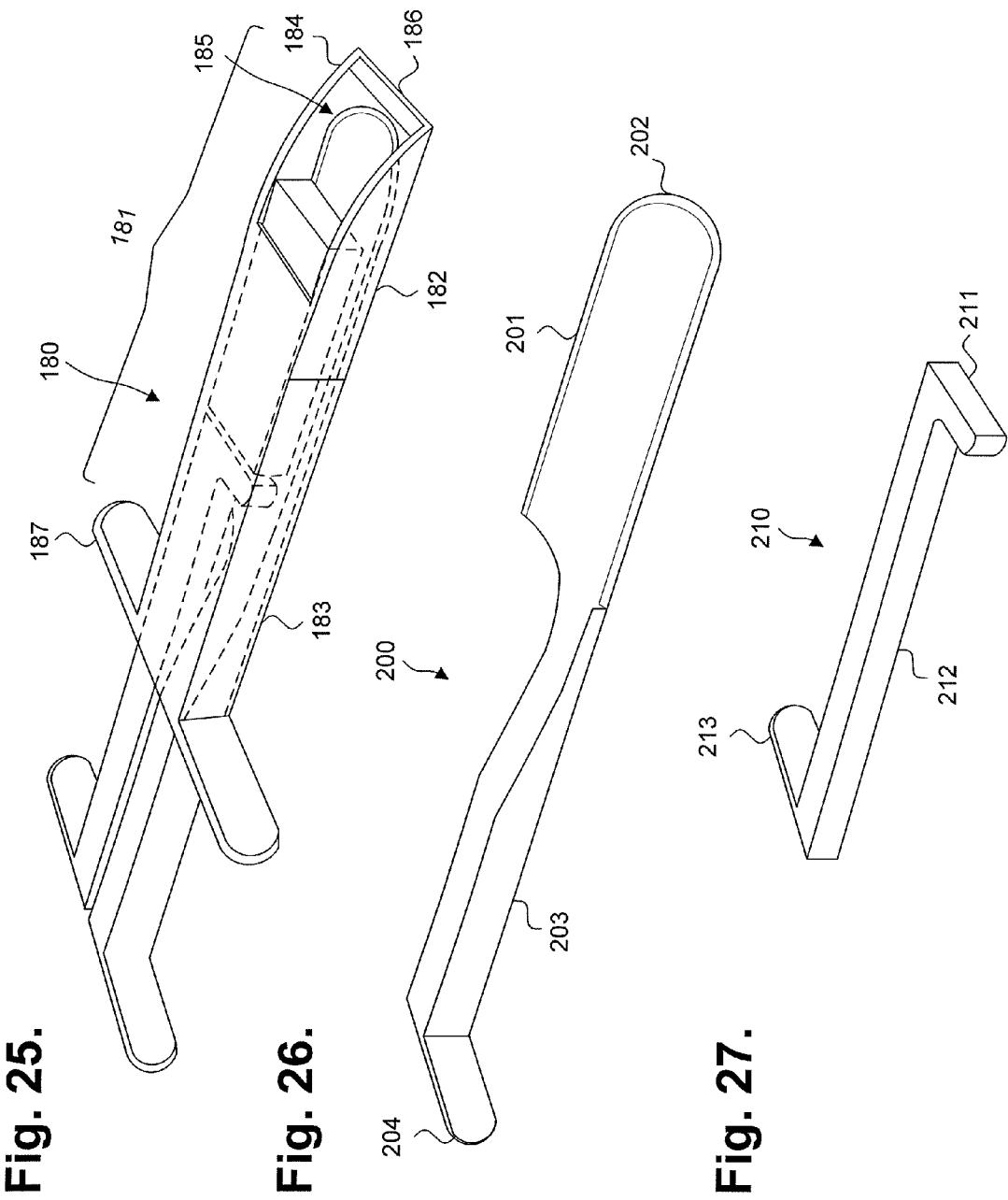

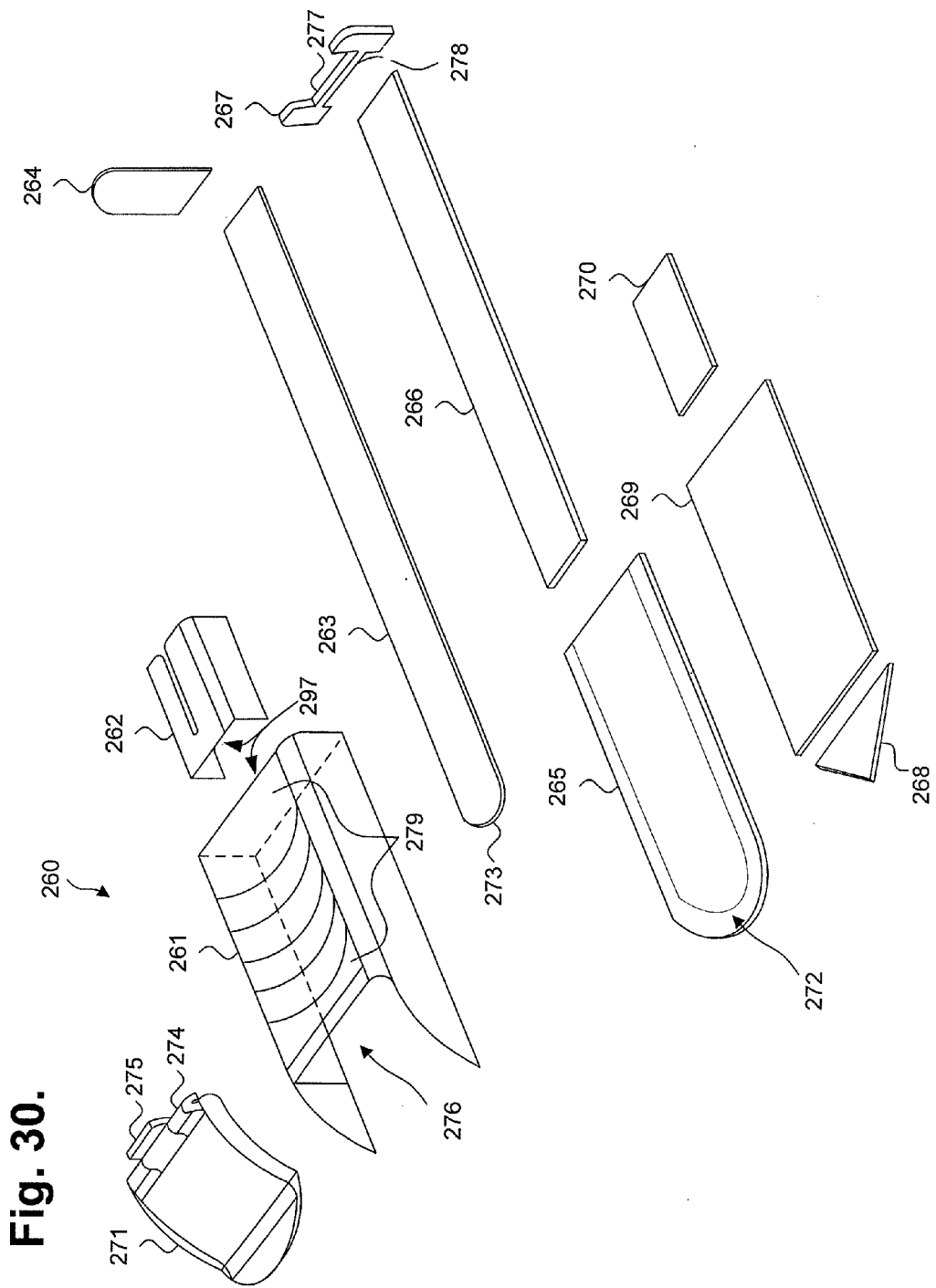

METHOD FOR CONSTRUCTING AN INSTRUMENT WITH A TWO-PART PLUNGER FOR SUBCUTANEOUS IMPLANTATION

CROSS-REFERENCE TO RELATED APPLICATIONS

This patent application is a continuation-in part of U.S. patent application Ser. No. 12/815,364, filed Jun. 14, 2010, pending which is a continuation application of Ser. No. 11/484,084, filed on Jul. 10, 2006 now U.S. Pat. No. 7,736,330, issued Jun. 15, 2010; which is a continuation-in-part of U.S. patent application Ser. No. 11/345,617, filed Feb. 1, 2006, now U.S. Pat. No. 7,780,625, issued Aug. 24, 2010; which is a continuation of U.S. patent application Ser. No. 11/025,770, filed Dec. 20, 2004, abandoned; which is a continuation of U.S. patent application Ser. No. 10/222,719, filed Aug. 15, 2002, abandoned; which is a continuation of Ser. No. 09/644,666 filed on Aug. 24, 2000 now U.S. Pat. No. 6,436,068, issued Aug. 20, 2002, the priority dates of which are claimed and the disclosures of which are incorporated by reference.

FIELD

The present invention relates in general to methods for subcutaneous implantation and, in particular, to methods for constructing an instrument with a two-part plunger for subcutaneous implantation.

BACKGROUND

Health care assessment includes the review and analysis of physiometry collected and recorded by electronic data sensors. The type and quality of physiometry can depend upon the type and location of sensor used. External sensors, such as thermometers, blood pressure cuffs, heart rate monitors, and the like, are limited in the kinds of information, which they are able to collect, and can encumber the patient. Implantable in situ sensors can provide a direct stream of recorded physiometry, but are invasive and require surgical implantation.

Recent advances in microchip technology have created a new generation of highly integrated, implantable monitors, sensors and medical devices, such as implantable cardioverter defibrillators, pacemakers, and insertable loop recorders. For instance, PCT Publication Nos. WO/2000/004945, to Habib et al., published Feb. 3, 2000, and WO/2000/004946, to Habib et al., published Feb. 3, 2000, respectively describe an implantable sensor chip and treatment regiment, the disclosures of which are incorporated by reference. Each sensor chip can collect and transmit physiometric data by wireless telemetry to a receiver external to a body. Similarly, the emerging Bluetooth wireless communication standard, described at http://www.bluetooth.com/developer/specification/specification.asp, proposes a low cost, small form factor solution for short range data communications, potentially suitable for use in implantable sensor technology.

Nevertheless, microchip sensors must still be implanted via some form of surgical procedure with the need to provide a sterile field, surgical staff, and surgical risks. Minimally invasive implantation using large bore needles or flat-edged blades is impracticable because sensors, particularly when embodied using microchip technology, favor a prismatic shape with substantially rectangular cross sections that are incompatible with circular bores.

As well, large bore needles can core out flesh, skin, or hide, when used in animals, as the instruments are inserted subcutaneously, which creates a risk of injury, scarring, and infection. Additionally, cored flesh trapped within the needle's bore can clog or interfere with correct implant placement. Moreover, wider-tipped instruments, such as a hollow point chisel, can potentially cause tearing, gouging, or similar injury due to the width of the cutting edge.

Also, achieving a desired subcutaneous depth for implant placement can be difficult using a large bore needle. Typically, a plunger pushes an implant through the needle and into the recipient's tissue. The tip of the large bore needle creates an opening conformably surrounding the needle inserted in the tissue. Prior to placing the implant, the needle must be withdrawn to create space, which can be risky and tedious. A physician must carefully withdrawal the needle to create a sufficient space for the implant while ensuring that the needle is not completely withdrawn. Otherwise, another incision must be made.

Further, an incising tool can extend the opening to create space for the implant to prevent withdrawal of the needle. Once the large bore needle is inserted into the recipient, the incising tool is introduced and an extension of the opening is cleared. Subsequently, the incising tool is removed and a plunger is introduced. The plunger pushes the implant into the extended opening without moving or repositioning the needle. Separate uses of the incising tool and plunger can contaminate the environment by exposing the implant to the external environment and can create a risk of infection. Additionally, the separate tools can be difficult to maneuver and may require assistance from a further physician or technician.

In addition, although current surgical implantation approaches attempt to minimize the size of incision and degree of invasiveness, implantation is, at best, costly, time-consuming, traumatic, requires multiple instruments and maneuvers, and potentially risky to the patient. For example, anesthetizing is conventionally performed using a topical or local anesthetic agent on the implantation site.

Subcutaneous implantable sensors offer the best compromise between in situ sensors and external sensors and are potentially insertable with a simple injection, rather than surgical procedure. These sensors are typically implanted below the dermis in the layer of subcutaneous fat. Several approaches to the subcutaneous implantation of solid materials have been described.

An insertion and tunneling tool for a subcutaneous wire patch electrode is described in U.S. Pat. No. 5,300,106, to Dahl et al., issued Apr. 5, 1994. The tunneling tool includes a stylet and a peel-away sheath. The tunneling tool is inserted into an incision and the stylet is withdrawn once the tunneling tool reaches a desired position. An electrode segment is inserted into the subcutaneous tunnel and the peel-away sheath is removed. Although providing a tool for subcutaneous implantation, the Dahl device requires an incision into the subcutaneous fat layer and forms an implantation site larger than the minimum sized required by the electrode segment. Further more, the cylindrical bore precludes the injection of non-conforming solid sensors or materials. As well, external exposure to the inside of the peel-away sheath with risk of injury are possible when the stylet is removed.

An implant system for animal identification that includes a device for implanting an identification pellet in a fat layer beneath the hide or skin of an animal is described in U.S. Pat. No. 4,909,250, to Smith, issued Mar. 20, 1990. The device includes a curved needle-like tube that terminates at a tapered, sharpened point. An elongated, flexible plunger is slidably received within the needle-like tube. The pointed tip is inserted through the hide or skin and the plunger is actuated to drive the identification pellet from the tip into the fat layer. However, the Smith device uses an oversized open bore, which can cause coring of the hide or flesh and the device must be partially withdrawn to implant the identification pellet.

A trocar for inserting implants is described in PCT Publication No. WO/1999/053991, to Peery, published Oct. 28, 1999. An implant retention trocar includes a cannula for puncturing the skin of an animal and an obturator for delivering the implant. A spring element received within the cannula prevents an implant from falling out during the implant process. The cannula has a distal tip design, which causes a minimum of trauma and tearing of tissue during implant insertion. However, the distal tip design is specifically directed to cannulas having a substantially circular bore and thereby limits the size and shape of implant, which can be inserted through the Clarke trocar. Further, the implant is delivered into the tissue via the obturator directly adjacent to the cannula, rather than a further distance from the cannula. Deeper implantation of the implant requires use of a separate clearing tool, which risks misalignment of the cannula.

An instrument for injecting implants through animal hide is described in U.S. Pat. No. 5,304,119, to Balaban et al., issued Apr. 19, 1994. The instrument includes an injector having a tubular body divided into two adjacent segments with a hollow interior bore. A pair of laterally adjacent tines extends longitudinally from the first segment to the distal end of the tubular body. A plunger rod has an exterior diameter just slightly larger than the interior diameter of the tubular body. With the second segment inserted beneath the animal hide, the push rod is advanced longitudinally through the tubular body, thereby pushing the implant through the bore. As the implant and rod pass through the second segment, the tines are forced radially away from each other, thereby dilating or expanding the incision, and facilitating implant. The instrument is removed from the incision following implantation. Though avoiding the coring of animal hide or flesh, the instrument forms an implantation site larger than the minimum sized required by the implant and causes potentially damaging compaction of the implant against the laterally adjacent times during implant delivery. Additionally, the implant is merely advanced into the animal hide or flesh without first clearing a pathway in the animal hide or flesh. Use of a trocar or other clearing device to clear a pathway would require removal of the plunger rod and insertion of the trocar in the tubular body.

Therefore, there is need for a non-surgical instrument and method for subcutaneous implantation of sensors and solid materials that preferably does not require an incision preparatory to instrument insertion.

There is a further need for a subcutaneous implantation instrument and method capable of implanting sensors and other solid materials that are not readily disposed to implantation through a substantially circular bore. Moreover, there is a further need for a subcutaneous implantation instrument and method which is minimally invasive, preferably creating the smallest needed implantation site, and capable of implantation without exposing the implant to longitudinal stresses.

There is a still further need for an implantation instrument that provides a progressive widening of an implantation site. Such progressive widening would facilitate the use of wider-tipped instruments that provide sufficient girth to admit implantable sensors and medical devices with lowered patient trauma. Preferably, such an instrument would include provision for application of an anesthetic agent.

There is yet a further need for an implantation instrument with a multi-part plunger that allows precise subcutaneous dissection of an implant site without requiring risky repositioning of a needle tip or introduction of a separate clearing tool in situ.

SUMMARY

An implantation instrument and method of use for implanting sensors and other solid materials in a subcutaneous or other site is provided. As used herein, "subcutaneous" refers generally to those implantation sites located within a body below the skin. The implantation instrument consists of an incising shaft attached to a syringe body. The syringe body and incising shaft both define a substantially non-circular hollow bore for accommodating the sensor or solid material. The subcutaneous site is formed by a cutting edge on the distal end of the incising shaft. The subcutaneous site can be cleared using a clearing trocar slidably received within the hollow bore. The sensor or solid material is advanced through the hollow bore and delivered into the subcutaneous site. The depth of the subcutaneous site can be limited using a penetration limiting mechanism.

One embodiment provides a method for constructing an instrument with a two-part plunger for subcutaneous implantation. An incising body is formed by defining a non-circular coaxial bore and sharpening a distal bottom edge. A two-part plunger including a tongue blade assembly and a plunger assembly is constructed. The tongue blade assembly is constructed by sharpening a beveled end of a flat thin tongue blade and by affixing a straight tongue blade shaft to an end of the tongue blade opposite the beveled end. The tongue blade assembly has a length exceeding the coaxial bore. The plunger assembly is constructed by affixing a plunger to a plunger shaft on a distal end. The plunger assembly has a length exceeding the coaxial bore and is oriented adjacent to the tongue blade assembly. The two-part plunger is inserted through an end of the incising body.

A further embodiment provides a method for constructing an instrument with a two-part plunger for subcutaneous implantation. An incising body is formed by including an incising shaft and a syringe body. The incising shaft is formed by defining a cavity located along a longitudinal axis and including a cutting edge formed on a distal end. The syringe body is formed by defining a bore extending along the longitudinal axis and having a circumference smaller than the cavity. The syringe body is affixed on a proximal end of the incising shaft with the bore aligned with a portion of the cavity. A two-part plunger including a tongue blade assembly and a plunger assembly is assembled. The tongue blade assembly is constructed by sharpening a beveled end of a tongue blade sized to fit within the cavity and by affixing the tongue blade to a straight tongue blade shaft sized to fit within the bore. The plunger assembly is constructed by affixing a plunger sized to fit within the cavity to a plunger shaft sized to fit within the bore. The plunger assembly is oriented above the tongue blade assembly. The two-part plunger is inserted through an end of the incising body.

A further embodiment provides a method for subcutaneous implant via an instrument with a two-part plunger. An incision is generated in a recipient by inserting a sharpened cutting edge formed on an end of an incising body. The incising body defines a non-circular coaxial bore in which an implant is housed and a bore opening. The incising body further houses a two-part plunger that includes a tongue blade assembly and a plunger assembly and is contained within the coaxial bore. A tunnel is formed as an extension of the incision by pushing the tongue blade assembly partially through the coaxial bore and the bore opening of the incising body. The tongue blade assembly has a length exceeding the coaxial bore. The implant is urged through the bore opening and into the tunnel via the plunger assembly, which has a length exceeding the coaxial bore.

A further embodiment provides an implantation device assembly. An incising body defines a non-circular coaxial bore and includes a cutting edge formed on a distal end. A two-part plunger is non-fixedly contained within the coaxial bore and includes a tongue blade assembly and a plunger assembly. The tongue blade assembly is provided on a bottom surface of the coaxial bore and includes a tongue blade shaft and a thin tongue blade with a sharpened clearing edge on a distal end. The tongue blade assembly has a length exceeding the coaxial bore. The plunger assembly has a length exceeding the coaxial bore and includes a plunger shaft and a plunger affixed on a distal end. The plunger is slidably positioned on a top surface of the tongue blade. An implant is positioned within the coaxial bore on top of the tongue blade.

One principal value of such a subcutaneous implantation instrument and method would be to enable the subcutaneous insertion of implantable objects and devices, such as sensors, without an operating room or special procedures room. In essence, the subcutaneous implantation instrument and method reduce insertion of implantable objects and devices having non-conforming shapes to be the functional equivalent of an injection.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

BRIEF DESCRIPTION OF THE DRAWINGS

FIGS. 5A-D are transverse cross-sectional views of the implantation instrument illustrating, by way of example, various bore configurations;

FIG. 6 is a segmented side view of a clearing trocar;

FIG. 7 is a segmented side view of a pushing stylet;

FIGS. 10A-10C are perspective views of cutting edges formed on distal edges of incising shafts, in accordance with further embodiments;

FIG. 11 is a longitudinal cross-sectional view of a subcutaneous implantation instrument in accordance with a further embodiment;

FIG. 12 is a top plan view of the subcutaneous implantation instrument of FIG. 11;

FIGS. 13-15 are transverse cross-sectional views of the dissecting tool assembly of FIG. 11;

FIG. 25 is a perspective view of an implantation instrument with a side-by-side two-part plunger, in accordance with a further embodiment;

FIG. 26 is a perspective view of the tongue blade assembly of the implantation instrument of FIG. 25;

FIG. 27 is a perspective view of the plunger assembly of the implantation instrument of FIG. 25;

FIG. 30 is an exploded perspective view of the instrument for implanting sensors or solid materials in a subcutaneous or other tissue location shown in FIG. 29;

DETAILED DESCRIPTION

Figure 1:
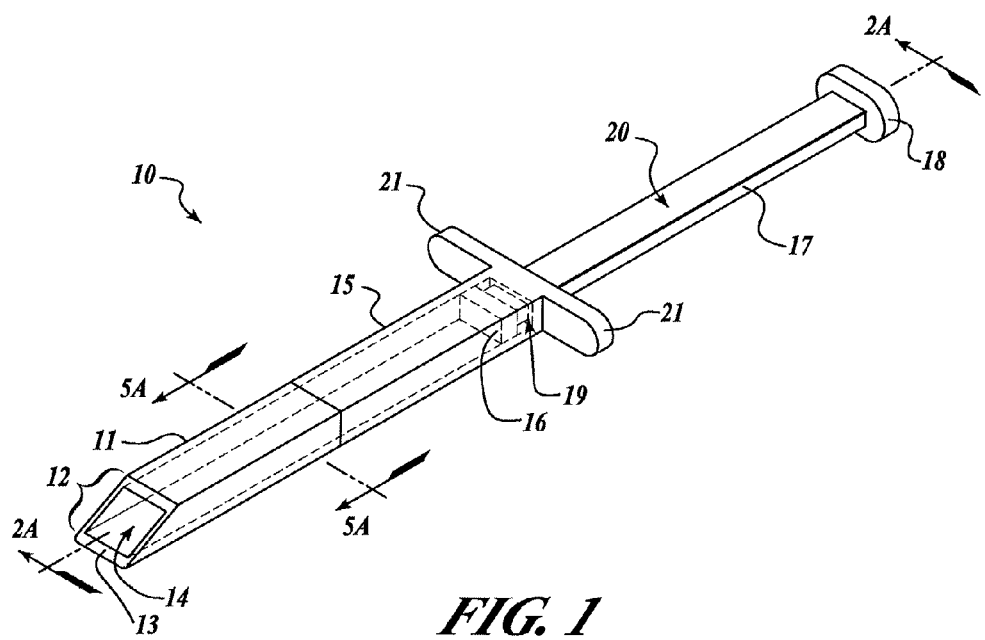
FIG. 1 is a perspective view of an instrument for implanting sensors or solid materials in a subcutaneous or other tissue location in accordance with the present invention.

FIG. 1 is a perspective view of an instrument 10 for implanting objects in a subcutaneous or other tissue location in accordance with the present invention. The implantation instrument 10 consists of two principal groups of components, an incising body consisting of an incising shaft 11 and a syringe body 15, and a delivery assembly consisting of a plunger assembly 20. The instrument 10 can be used to non-surgically implant an object, such as a sensor or monitor, medical therapeutic device, or other solid or semi-solid object. The delivery assembly is received into the syringe body bore by sliding the plunger assembly 20 through proximal bore opening 19. An implantable object is received into the syringe body bore. During an implant procedure, the implantable object is deployed into the incising shaft and thence inserted subcutaneously into an implantation site by progressive distal urging of the plunger assembly 20, as further described below beginning with reference to FIG. 18.

The incising shaft 11 is a hollow point chisel that is formed with a beveled and rounded tip 12 that tapers into a surgically sharp cutting edge 13 formed on a distal edge. The beveled tip 12 includes a distal bore opening 14 through which the implantable object is delivered into the implantation site.

The implantable object includes medical monitoring and diagnostic devices, such as an implantable physiometry sensor, and non-medical monitoring devices, such as an environmental or activity monitor. Such sensors generally record data for subsequent retrieval and can be autonomously triggered or triggered manually by the implant recipient. One implantable sensor microchip suitable for use in the present invention is described in PCT Publication No. WO/2000/004945, to Habib et al., published Feb. 3, 2000, the disclosure of which is incorporated by reference. Such a sensor could be used for monitoring and collecting physiological or chemical measures. A further implantable monitoring device suitable for use is the Reveal insertable loop recorder, manufactured by Medtronic, Inc., Minneapolis, Minn., which is an implantable heart monitor for diagnosing the causes of syncope and other transient heart symptoms involving rhythm-related disorders, as described in U.S. Pat. No. 5,331,966, issued Jul. 26, 1994 to Bennett et al; U.S. Pat. No. 6,230,059, issued May 8, 2001 to Duffin; and U.S. Pat. No. 6,317,626, issued Nov. 13, 2001 to Warman, the disclosures of which are incorporated by reference. Other medical monitoring and diagnostic devices are possible.

The implantable object also includes non-sensor-type implantable medical devices, including implantable medical devices for therapeutic uses, such as administering cardiac pacing or rhythm therapy; providing neural, muscle, or organ stimulation; cancer treatment; and delivering or dosing medication. As well, the present invention has equal applicability to implantation of other types of non-medical sensors, including location and identification sensors, such as radio frequency identification (RFID) tags. Such sensors could include data transmitters with which to exchange recorded data and instructional signals.

Finally, the implantable object can include solid or semi-solid materials, such as a gelatinous drug bolus. In one embodiment, the implantable object has approximate dimensions of 5 mm by 10 mm by 20 mm, although other dimensions can be equally suitable. The critical dimension is the cross-sectional profile, that is, the height and width, of the implant, which must conform to passage through the syringe body and incising shaft bores. Other non-linear, prismatic shapes are equally usable provided the implantable object can fit within the confines of the syringe body and incising shaft bores. The implant could also be folded or compacted to minimize the cross-sectional profile with the implant unfolding or expanding upon implantation. As well, the implant is preferably protected against damage by encasement within, for example, a mannitol pellet in the case of a solid drug delivery system or epoxy in the case of an implantable sensor or medical device. Other sizes, shapes, and types of non-liquid implantable objects are possible.

The incising shaft 11 is fixably attached to the syringe body 15 through frictional, adhesive, or preformed constructive means, as is known in the art. Both the incising shaft 11 and syringe body 15 define a substantially non-circular hollow bore extending continuously along a shared longitudinal axis, as further described below with reference to FIGS. 5A-D.

The plunger assembly includes a plunger 16, an interconnecting plunger shaft 17 and a plunger end piece 18. The plunger 16 is conformably shaped to fit within the syringe body bore. The plunger end piece 18 facilitates deployment of the plunger assembly through the syringe body bore and is preferably shaped to fit a thumb or palm impression. In a further embodiment, the non-circular hollow bore opens to the distal end of the incising shaft 11 and extends only partly through to thereby form a cavity, rather than a tube, but with provision for the sliding of the plunger shaft 17.

In the described embodiment, the implantation instrument 10 is designed for inexpensive and disposable use utilizing low-cost, sanitizable materials. The implantation instrument 10 can be used for out-patient or non-surgical subcutaneous implant and insertion of an implantable object, as further described below beginning with reference to FIG. 18. The incising shaft 11 can be fashioned from surgical grade stainless steel and has the approximate dimensions of approximately 10 mm by 5 mm in cross section. The incising shaft 11 is approximately 50 mm long and the length can be varied to accommodate different implantation depths. The plunger 16 is formed from plastic and rubber and preferably forms a watertight seal within the syringe body bore and has the approximate dimensions of approximately 8 mm by 3 mm in cross section. The plunger shaft 17 and plunger end piece 18 are formed from plastic or similar material. Other materials, as would be recognized by one skilled in the art, could be substituted.

In a further embodiment, the syringe body 15 and plunger assembly can be replaced by an automated injection system, such as used with immunization injection guns or similar devices. These devices typically employ compressed air or other inert gases to administer medication in lieu of manual plungers. Other automated variations include spring-loaded and similar mechanical injection systems. The incising shaft 11 is fixably attached to the automated injection system which functions as a delivery mechanism in place of the syringe body 15 and plunger assembly. Thus, the implant would be pushed through the incising shaft bore using the compressed air or gas, or mechanical equivalent.

Figure 2A:
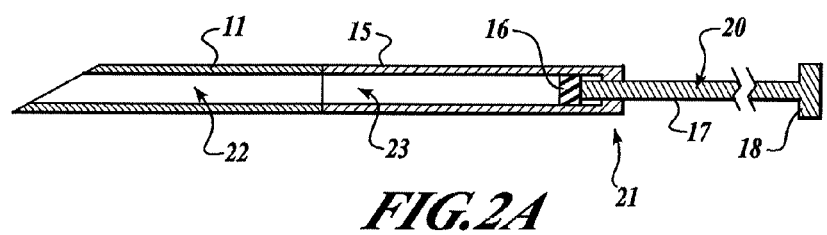
FIG. 2A is a longitudinal cross-sectional view of the implantation instrument with a straight incising shaft.

FIG. 2A is a longitudinal cross-sectional view of the implantation instrument 10 with a straight incising shaft 11. The hollow bore defined by both the incising shaft 11 and the syringe body 15 runs along a common shared axis. The incising shaft bore 22 is sized to allow the implant to advance smoothly into the implantation site under the forward lateral urging of the plunger assembly 20. The syringe body bore 23 must be at least as large as the incising shaft bore 22, but can be slightly larger to accommodate lubricants, anesthetizing agents, or similar coatings, such as mannitol, applied over the implantable object.

The syringe body 15 preferably includes a circular collar 21, pair of winglets, ears, or eyelets, or similar structure, optionally formed on a proximal end of the syringe body 15 to assist a user in depressing the plunger assembly 20.

Figure 2B:
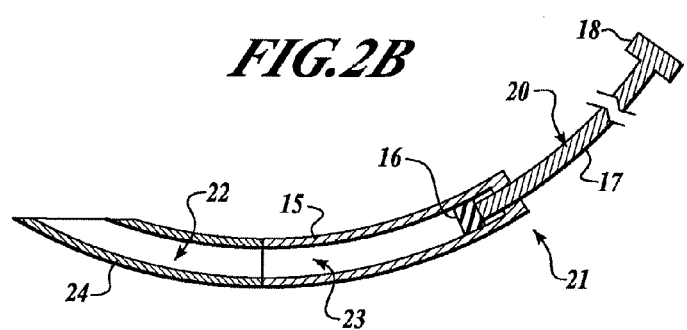
FIG. 2B is a longitudinal cross-sectional view of the implantation instrument with a curved incising shaft.

FIG. 2B is a longitudinal cross-sectional view of the implantation instrument with a curved incising shaft 24. The curved incising shaft 24, as well as the syringe body 15 and related components, are shaped into a substantially continuous curve along the ventral side. The curvature helps regulate the penetration depth of the incising shaft and, in the described embodiment, has an arc of approximately 20 degrees.

Figure 3:
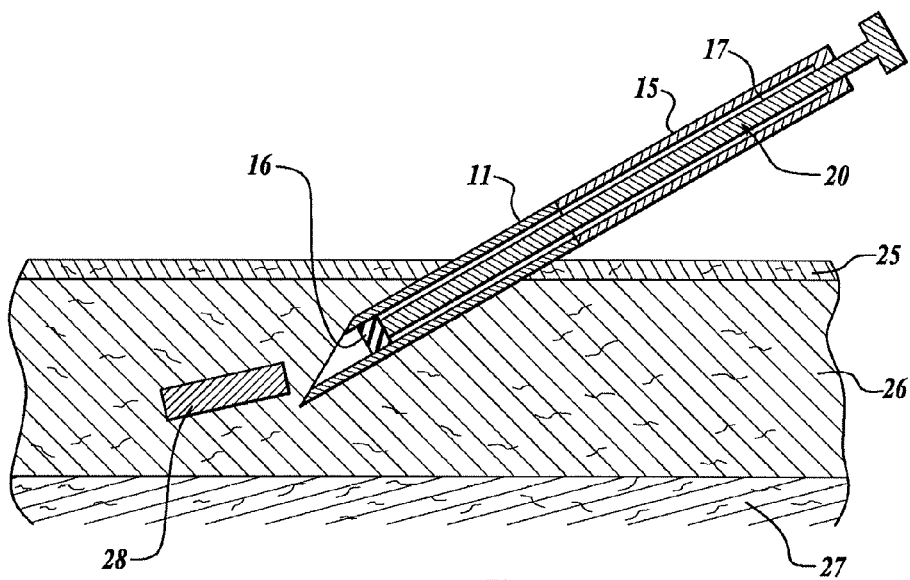
FIG. 3 is a diagrammatic view illustrating the implantation of an object into a subcutaneous site.

FIG. 3 is a diagrammatic view illustrating the implantation of an implantable object 28, including a sensor, implantable medical device, such as an implantable cardioverter defibrillator, pacemaker, or insertable loop recorder, or other solid material into a subcutaneous site. Other implantable objects are possible. During implantation, the incising shaft 11 is inserted through the dermis 25 and guided into the layer of subcutaneous fat 26, above the layer of muscle 27, to a subcutaneous implantation site. The implantable object 28 is fed through the proximal bore opening 19 or received through the distal bore opening of the syringe body 15. The implantable object 28 is then further advanced through the syringe body bore 23 and the incising shaft bore 22 by the plunger 16 into the subcutaneous site. Note that although the foregoing view illustrates an implant into the subcutaneous fat layer, one skilled in the art would appreciate that subcutaneous implantation locations are not strictly limited to the subcutaneous fat layer and are generally termed as those implantation locations situated subdurally within a body under the skin. Accordingly, subcutaneous implantation sites further include locations that are intramuscular and submuscular, or within a body cavity, including intrathoracic.

Figure 4A:
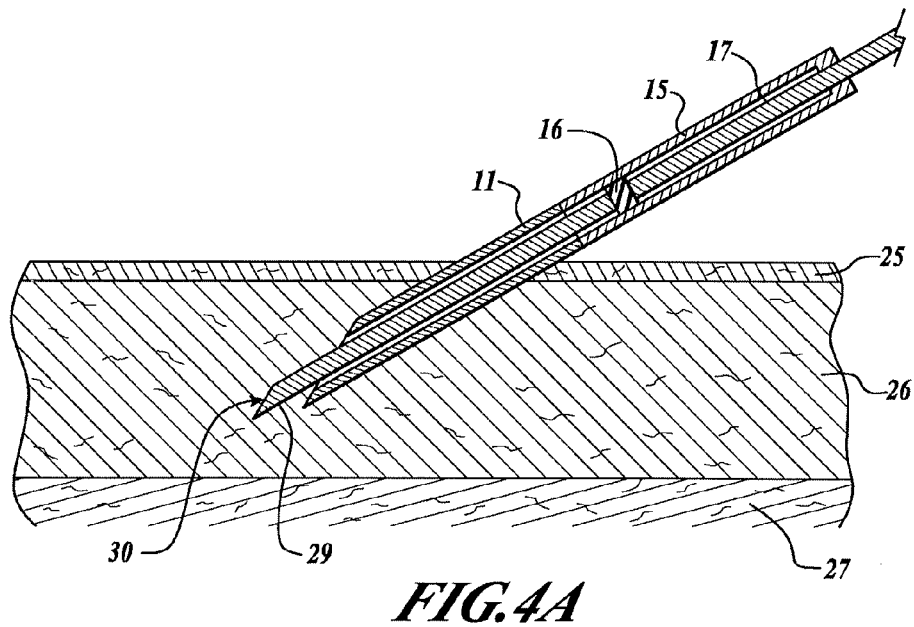
FIG. 4A is a diagrammatic view illustrating the clearing of a subcutaneous site using the implantation instrument fitted with a clearing trocar in accordance with a further embodiment.

FIG. 4A is a diagrammatic view illustrating the clearing of a subcutaneous site using the implantation instrument 10 fitted with a clearing trocar 29 in accordance with a further embodiment. The clearing trocar 29, as further described below with reference to FIG. 6, is mounted to its own handle or plunger assembly and has a sharp cutting tip 30 for optionally clearing a subcutaneous site prior to delivery of the implant.

Prior to implantation, the clearing trocar 29 is slidably received into the syringe body 15 and is advanced until the cutting tip 30 is even with the proximal bore opening 19 of the incising shaft 11. During operation, the incising shaft 11 and clearing trocar 29 are inserted through the dermis 25 and guided into the layer of subcutaneous fat 26, above the layer of muscle 27.

The cutting edge 13 of the beveled tip 12 makes an entry incision through the dermis 25 and is laterally pushed into the subcutaneous fat 26 until the cutting edge 13 is adjacent to the subcutaneous site. The clearing trocar 29 is then urged through the subcutaneous fat 26 by advancement of its handle or plunger assembly to prepare the implantation site for delivery of the implantable object 28, including an implantable sensor, medical device, or other solid material. The clearing trocar 29 is then withdrawn from the subcutaneous site and out of the implantation instrument 10.

Figure 4B:
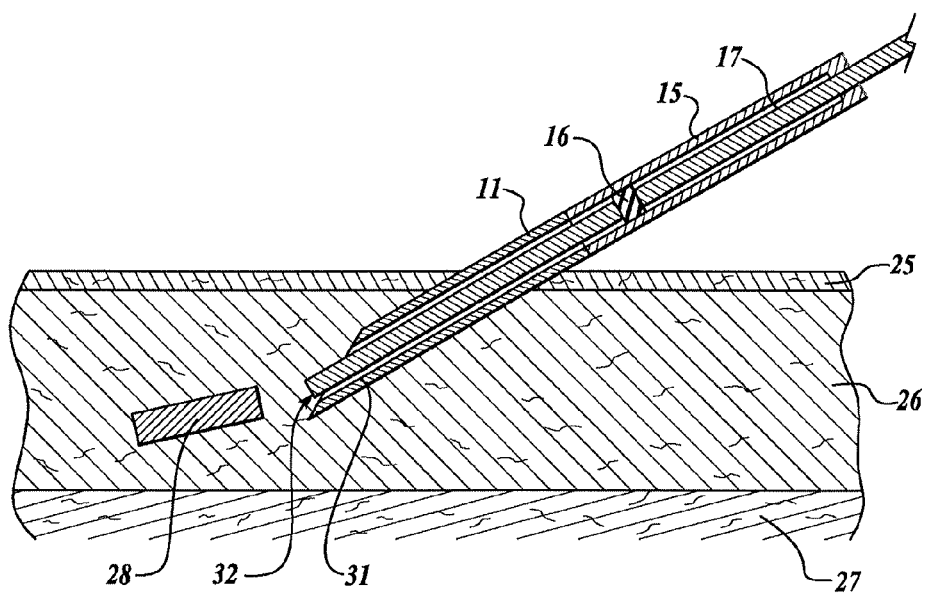
FIG. 4B is a diagrammatic view illustrating the subcutaneous implantation of an object using the implantation instrument fitted with a pushing stylet in accordance with a further embodiment.

FIG. 4B is a diagrammatic view illustrating the subcutaneous implantation of an implantable object 28 using the implantation instrument 10 fitted with a pushing stylet 31 in accordance with a further embodiment. The pushing stylet 31, as further described below with reference to FIG. 7, has a blunt tip 32 for advancing the implantable object 28 through the syringe body bore 23 and incising shaft bore 22 and into the subcutaneous site. The cross section of the pushing stylet 31 closely conforms to the incising shaft bore 22 while the plunger 16 closely conforms to the syringe body bore 23. The pushing stylet 31 thus extends the reach of the plunger assembly 20 and allows the syringe body bore 23 to have a different cross-section than the incising shaft bore 22.

The pushing stylet 31 is used while the incising shaft 11 is in situ in the subcutaneous layer 26. Prior to delivery, the implantable object 28 is fed through the proximal bore opening 19 of the syringe body 15 and further advanced within the syringe body bore 23 by contact with the plunger 16. The pushing stylet 31 is slidably received into the syringe body 15 and is advanced until the blunt tip 32 contacts the implantable object 28. During operation, the implantable object 28 is urged through the incising shaft bore 22 by the pushing stylet 31 and into the subcutaneous site by advancement of the plunger assembly. Upon delivery of the implantable object 28 into the subcutaneous site, the incising shaft 11 and pushing stylet 31 are withdrawn.

Although operation of the implantation instrument 10 is described with reference to the implantation of sensors or solid materials into a subcutaneous site situated within the layer of subcutaneous fat 26, implantations could also be effected in other subcutaneous, intramuscular, intraperitoneal, intrathoracic, intracranial, intrajoint, as well as other organ or non-subcutaneous sites, as would be recognized by one skilled in the art. In addition, the foregoing procedure could be modified to forego the use of the clearing trocar 29 for small implantable objects 28. The clearing effect of the clearing trocar 29 can be approximated by use of the incising shaft 11 alone whereby the incising shaft 11 is inserted into the subcutaneous site and then withdrawn by reverse deployment, thereby forming a slightly overwide implantation site.

The operations of subcutaneous implantation can be carried out over a plurality of sites and with the same or different implantable objects 28. Similarly, several implantable objects 28 could be implanted at the same subcutaneous site during a single implantation operation.

Inclusion of both the clearing trocar and the pushing stylet in the implantation instrument can help reduce risk of inadvertent injury during implant and post-implant risk of infection when separate clearing trocar and pushing stylet components are separately used. A cooperative two-part plunger replaces the separate trocar and pushing stylet and, in one embodiment, is packaged inside the syringe with the implant. The two-part plunger includes a tongue blade assembly and a plunger assembly, which are each partially positioned within the incising body of the implantation instrument to maintain a sterile environment for implantation.

Figure 21:
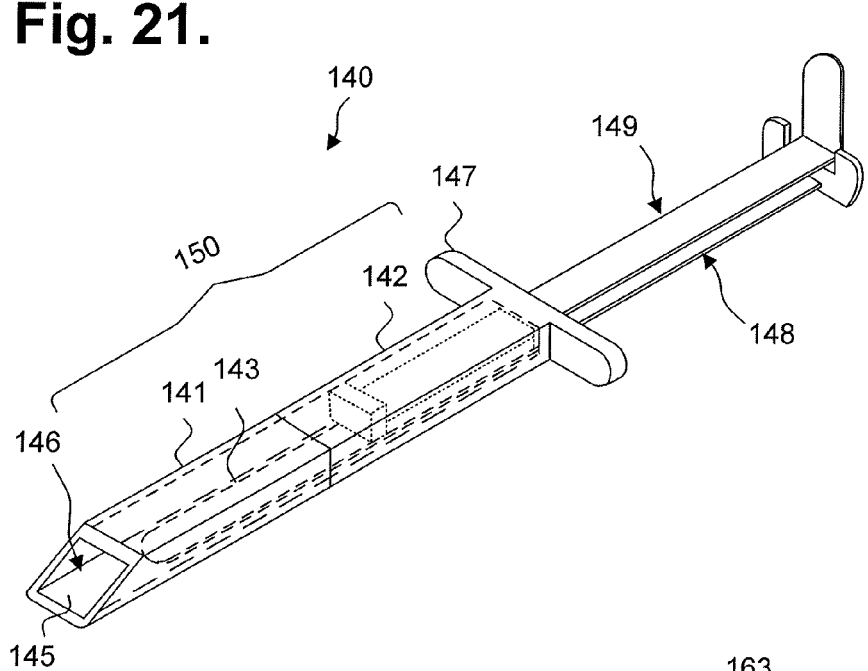
FIG. 21 is a perspective view of an implantation instrument with a stacked two-part plunger, in accordance with a further embodiment.

The two-part plunger can reduce the risk of infection and simplifies use by a physician. FIG. 21 is a perspective view of an implantation instrument 140 with a stacked two-part plunger, in accordance with a further embodiment. The incising body 150 of the implantation instrument 140 includes an incising shaft 141 and a syringe body 142, as described earlier in detail above with reference to FIG. 1. A proximal end of the incising shaft 141 is fixedly attached to the syringe body 142 through frictional, adhesive, or preformed constructive means. In a further embodiment, the incising body can be a single unitary member (not shown) that combines the incising shaft and the syringe body. Together, the incising shaft 141 and syringe body 142 define a coaxial non-circular bore 143 that receives an implantable sensor or monitoring device, as described above in further detail with reference to FIG. 1. The bore 143 extends from a bore opening on one end of the incising shaft 141 continuously through an open end of the syringe body 142. More specifically, the bore 143 is continuously formed when the incising shaft 141 and the syringe body 142 are positioned end-to-end. In one embodiment, the bore has approximate cross-sectional dimensions less than 10 mm by 5 mm; however, other dimensions are possible, depending on implant size. In a further embodiment, the bore can vary in cross-sectional dimensions, as described in further detail below with reference to FIG. 29.

A beveled tip is formed at the bottom of the incising shaft 141 on a distal end and at a distal bore opening 146, opposite the syringe body. The beveled tip includes a beveled cutting blade that can be formed to conformably follow an inside contour of the bore and to longitudinally taper into a sharp straight cutting edge 145 on a distal bottom edge of the incising shaft 141 with rounded ends on either bottom side of the edge. The straight cutting edge 145 with rounded ends prevents coring of skin and flesh when used in the implanting of sensors and other materials that require a large bore instrument. Also, the sharp cutting edge 145 can be formed as a right triangle blade, an arrowhead blade, a triangle blade, and a convex triangle blade. Other shapes and configurations of the cutting edge are possible. A circular collar 147, pair of winglets, ears, or eyelets, or similar structure, are optionally formed on a proximal end of the syringe body 142, opposite the cutting edge, to assist a user in gripping and depressing the plunger assembly 149.

Parts of, or the entire, incising shaft and syringe body can be made from surgical grade stainless steel, a durable plastic, such as Polyetheretherketone, or related materials. For example, a bottom surface of the incising shaft and syringe body can be made from stainless steel, while the remaining surfaces are made from durable plastic. The material used for the incising shaft and syringe body should be biocompatible and sterilizable. If single use is intended, the incising body can be prepackaged in sterile packaging.

Prior to implant deployment and up through the point of implant site dissection, the stacked two-part plunger is partially positioned within the bore of the incising body. During implant, the two-part plunger can be slidably moved to clear a pathway in the recipient's tissue using the tongue blade and position the implant into a cavity in the tissue using the plunger. Use of the two-part plunger maintains a sterile environment for implanting by minimizing exposure of the two-part plunger components to the ambient environment outside the sterile field.

Figure 22:
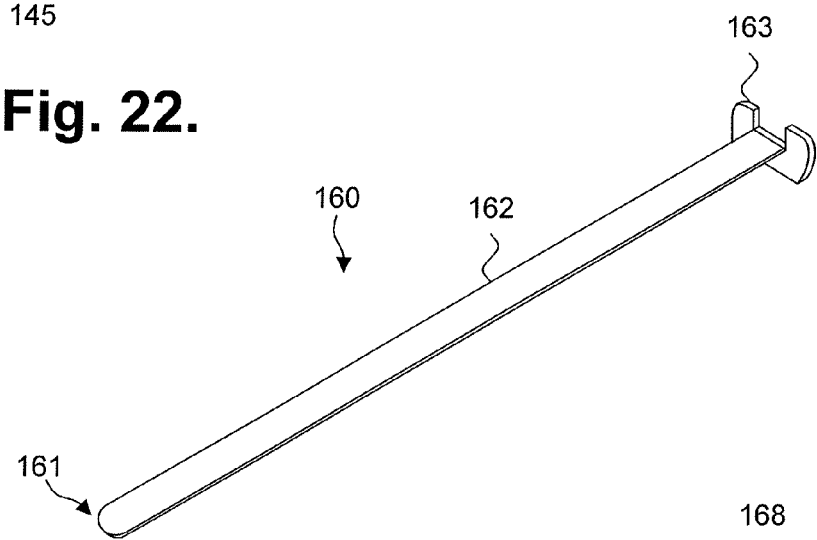
FIG. 22 is a perspective view of the tongue blade assembly of the implantation instrument of FIG. 21.

The stacked two-part plunger includes a tongue blade assembly 148 and a plunger assembly 149. FIG. 22 is a perspective view of a tongue blade assembly 160 for use in the implantation instrument of FIG. 21. The tongue blade assembly 160 includes a tongue blade end 161, a tongue blade shaft 162, and a tongue blade handle 163. The tongue blade shaft 162 has a flat surface with a sharpened clearing end 162, opposite the tongue blade handle 163, such that the clearing end 161 faces distally. The sharp clearing end 161 can have a convex shape or a flat shape (not shown) with a beveled tip forming a sharpened edge. During use, the tongue blade 161 clears a pathway through tissue as the tongue blade handle 163 is pushed distally and the tongue blade end 161 is urged beyond the tip of the incising shaft, thereby forming a cavity or "tunnel" into which the implant can be received. Tongue blade length is dependent on desired extended depth of incision, size of the implant, and length of the bore. When the tongue blade handle 163 is positioned against the syringe body in a deployed position, the tongue blade end 161 extends beyond the length of the bore, through the bore opening, and into the tissue. The tunnel formed is the length of the tongue blade end 161 extending beyond the bore opening.

The tongue blade shaft 162 can be circular or non-circular. The tongue blade handle 163 facilitates deployment of the tongue blade assembly through the incising body's bore. In one embodiment, the tongue blade handle can include a cutout 164 sized to receive the plunger assembly and guide the plunger assembly through the incising body.

Figure 23:
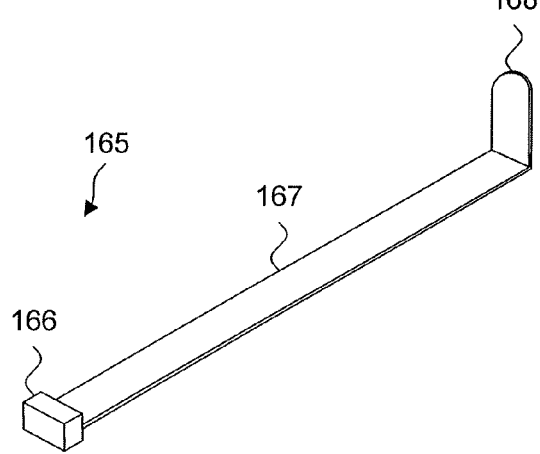
FIG. 23 is a perspective view of the plunger assembly of the implantation instrument of FIG. 21.

In the stacked two-part plunger configuration, the tongue blade assembly is positioned along a bottom surface of the bore, below the plunger assembly. Together, the tongue blade assembly and the plunger assembly are cooperatively operable to clear a path in the tissue and position the implant. FIG. 23 is a perspective view of a plunger assembly 165 for use in the implantation instrument of FIG. 21. Within the incising body, the plunger assembly 165 is positioned above the tongue blade assembly, which sits on a bottom surface of the bore. The plunger assembly has a plunger 166, plunger shaft 167, and plunger handle 168. The plunger 166 is sized to fit within the incising body above a top surface of the tongue blade and slidably moves by distal urging of the plunger handle 168. During deployment of the plunger assembly 165, the plunger 166 contacts the implant positioned on top of the tongue blade and urges the implant through the incising body and into a cavity formed in the tissue by the tongue blade. The stacked positioning of the tongue blade assembly and the plunger assembly is further discussed below with reference to FIG. 21.

The plunger shaft 167 can also be circular or non-circular. The plunger handle 168 facilitates movement of the plunger assembly within the bore formed by the syringe body and incising body. The plunger handle 168 can be sized and attached to fit within the cutout of the tongue blade handle 168.

Referring back to FIG. 21, the stacked two-part plunger is assembled for partial placement inside of the incising body 150. A portion of the tongue blade assembly fits on a bottom surface of the bore and freely slides along the surface to move in and out of the incising body. The plunger assembly is positioned above the tongue blade assembly, and the plunger assembly and the tongue blade assembly are axially aligned. During use, the tongue blade assembly and the plunger assembly are cooperatively operable. First, the tongue blade assembly can be deployed to clear a path or cavity in the tissue beyond the tip of the incising shaft. Next, the plunger is distally passed to move the implant into the cavity formed in the tissue using the tongue blade as a guide. Finally, the implant is positioned in the cavity and the tongue blade assembly and the plunger assembly are retracted.

Figure 28A:
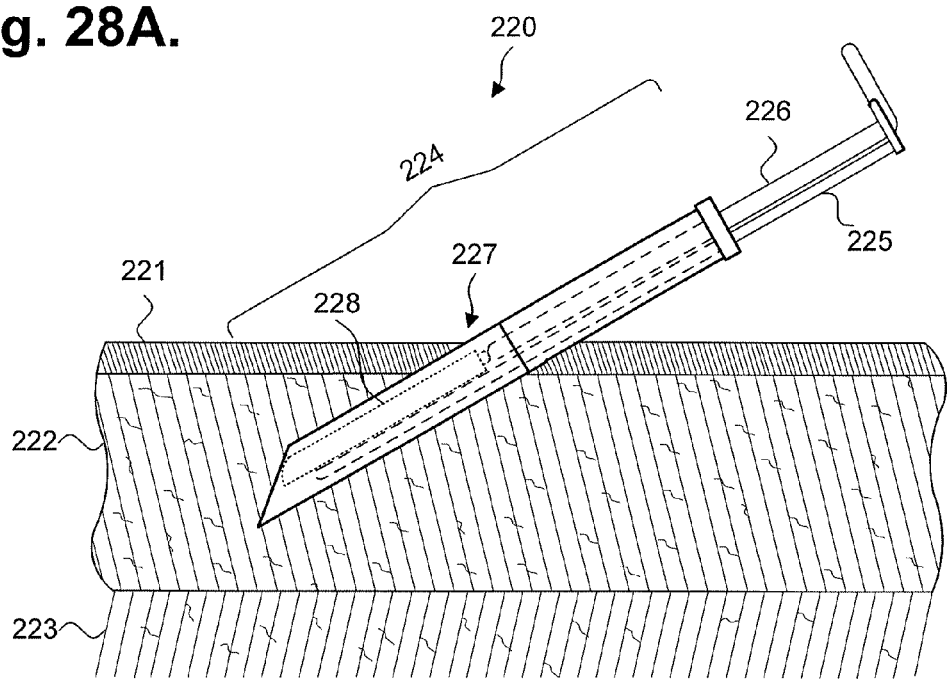
FIG. 28A is a diagrammatic view illustrating the dissecting of a subcutaneous site.

In a retracted position, the tongue blade assembly and the plunger assembly are moved away from the cutting edge of the incising shaft, as further discussed below with reference to FIG. 28A. Further, in a deployed position, the tongue blade assembly and the plunger assembly are distally deployed toward the cutting edge of the incising body until the tongue blade handle and the plunger handle respectively contact the circular collar 147 or a proximal end of the syringe body. Deployment of the tongue blade assembly and the plunger assembly is further discussed below with reference to FIGS. 28B-C.

In a further embodiment, the plunger assembly is positioned along a bottom surface of the bore and the tongue blade assembly is positioned above the plunger assembly. The tongue blade clears a path above the implant, which is urged by the plunger into a cavity formed in the tissue. Other configurations of the two-part plunger are possible.

The stacked two-part plunger can be made from surgical grade stainless steel, a durable plastic, such as Polyetheretherketone, rubber, or related materials, as well as from a combination of materials. In one embodiment, the tongue blade is formed from stainless steel, while the tongue blade shaft and tongue blade handle are formed from durable plastic. Alternatively, the plunger can be formed from rubber, while the plunger shaft and plunger handle are formed from durable plastic. Other materials and combinations of materials are possible.

Figure 24:
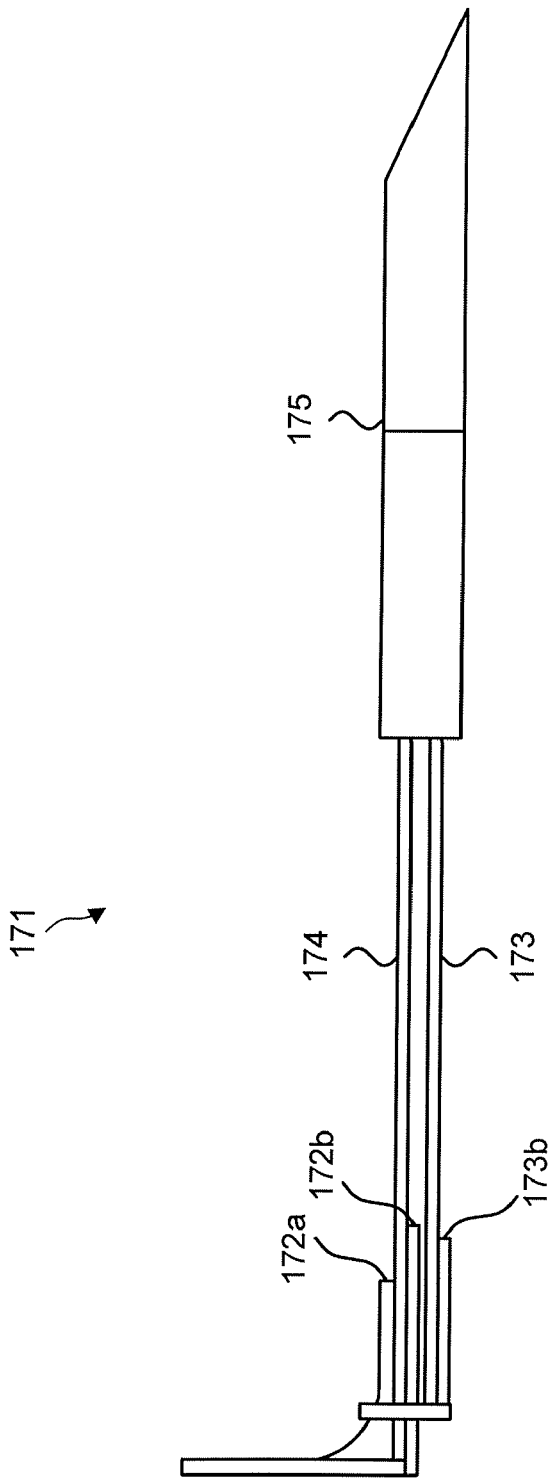
FIG. 24 is a side view of the implantation instrument of FIG. 21 with guide tracks.

Guide tracks can be utilized to enforce cooperative movement and prevent misalignment of the tongue blade assembly and the plunger assembly. FIG. 24 is a side view 170 of the implantation instrument 171 of FIG. 21 with guide tracks 172*a-c*. The guide tracks 172*a-c* facilitate the sliding of the tongue blade assembly 173 and plunger assembly 174 within the incising body 175. The guide tracks 172*a-c* can include ball and groove, guide shelves, rail and wheels, or support member and groove, which are formed on at least two of the incising body, tongue blade assembly, and plunger assembly. Other types of guide tracks are possible.

In one embodiment, one or more support members 172*a-c* are formed partially along a bottom surface of the plunger shaft and extend outward from the bottom surface. The tongue blade shaft includes corresponding grooves (not shown) that are sized to conformably receive the support members formed on the plunger shaft and allow movement of the tongue blade shaft back and forth along the plunger shaft. More specifically, movement of the tongue blade shaft and plunger shaft allow the tongue blade assembly and the plunger assembly to move in relation to one another as the support members slide back and forth within the grooves.

In a further embodiment, the two-part plunger has a side-by-side configuration. FIG. 25 is a perspective view of an implantation instrument 180 with a side-by-side two-part plunger, in accordance with a further embodiment. The implantation instrument 180 includes an incising body 181 within which the side-by-side two-part plunger can be slidably located. The incising body 181 is formed by a syringe body 183, which is fixedly attached to an incising shaft 182. The incising body 181 is discussed above in detail with reference to FIG. 1. In a further embodiment, the incising body 181 can be a single unitary member. A coaxial non-circular bore is longitudinally formed within the syringe body 183 and the incising shaft 182. The bore extends from a bore opening 185 on a distal end of the incising shaft 182 continuously through a proximal end of the syringe body 183. In one embodiment, the bore has an approximate cross-sectional dimension of 3 mm; however, other dimensions are possible. In a further embodiment, the bore can have different dimensions along the incising body.

A beveled tip 184 is formed on a distal end of the incising shaft 182 at a distal bore opening 185. The beveled tip 184 includes a beveled cutting blade that conformably follows an inside contour of the bore and tapers into a straight sharp cutting edge on a distal bottom end of the incising shaft 182 with rounded ends on either bottom side of the edge. The straight cutting edge with rounded ends prevents coring of skin and flesh when used in the implanting of sensors and other materials that require a large bore instrument. Additionally, the sharp cutting edge 186 can also be formed as a right triangle blade, an arrowhead blade, a triangle blade, and a convex triangle blade. Other configurations of the cutting edge are possible. A circular collar 187, pair of winglets, ears, or eyelets, or similar structure, are optionally formed on a proximal end of the syringe body 183, opposite the cutting edge 186, to assist a user in instrument use.

Parts of or the entire incising shaft and syringe body can be made from surgical grade stainless steel, a durable plastic, such as Polyetheretherketone, or related materials. For example, a bottom surface of the incising shaft and syringe body can be made from stainless steel, while the remaining surfaces are made from durable plastic. The material used for the incising shaft and syringe body should be biocompatible and sterilizable. Otherwise, if single use is intended, the incising body can be sterilized and prepackaged for convenient use.

The side-by-side two-part plunger is partially positioned within the bore of the incising body and can be slidably moved to clear a pathway or cavity in the tissue beyond the tip of the incising shaft and urge the implant into the cavity. Use of the two-part plunger provides a sterile environment for placement of the implant by minimizing exposure of the two-part plunger to the ambient environment. Further, the side-by-side two-part plunger facilitates efficient and convenient implantation by single insertion of tools and stable positioning of the instrument.

The side-by-side two-part plunger also includes a tongue blade assembly and a plunger assembly. FIG. 26 is a perspective view of a tongue blade assembly 200 for use in the implantation instrument of FIG. 25. The tongue blade assembly 200 includes a tongue blade 201, tongue blade shaft 203, and tongue blade handle 204. The tongue blade 202 is formed on one end of the tongue blade shaft 203, opposite the tongue blade handle 204. The tongue blade shaft 203 is a straight member that is shaped to fit within a portion of the bore. In a further embodiment, the tongue blade shaft 203 can be circular. A length of the tongue blade shaft 203 is dependent on desired depth for incision of the tissue, size of the implant, and length of the bore. Tongue blade shaft 203 width is dependent on the size of the bore and a width of the plunger assembly, specifically, the plunger shaft. A height of the tongue blade shaft 203 is gradually reduced and tapered on a distal end to form a transition onto the tongue blade 201.

The tongue blade 201 and the tongue blade shaft 203 can be formed as separate parts or as a single unitary member. The tongue blade 201 has a flat surface with a sharpened outer circumference 202 that can clear a pathway in the tissue when extended beyond the tip of the incising shaft. The outer edge of the tongue blade is convex in shape and can taper to form the sharpened cutting edge 202. A width of the tongue blade 201 can be larger than the tongue blade shaft and is dependent on a size of the bore, a size of the implant, and a desired width of incision. In one embodiment, the width of the tongue blade is sized to conformably fit within the bore of the incising body. Further, a length of the tongue blade 201 is dependent on a desired depth of incision, a length of the tongue blade shaft, and a length of the implant. Meanwhile, the height of the tongue blade 201 is dependent on a height of the bore and a size of the implant, which can be positioned on a top surface of the tongue blade. Other sizes and configurations of the tongue blade are possible.

The tongue blade handle 204 can be perpendicularly affixed to the tongue blade shaft to control movement of the tongue blade assembly out of and into the incising body through the bore opening. The tongue blade handle 204 is shaped to fit a thumb, finger, or palm impression for moving the tongue blade in and out of the incising body.

The tongue blade assembly cooperatively operates with the plunger assembly. FIG. 27 is a perspective view of a plunger assembly 210 for use in the implantation instrument of FIG. 25. The plunger assembly 210 includes a plunger 211, a plunger shaft 212, and a plunger handle 213. The plunger assembly 210 urges the implant distally through the bore and into a cavity formed in the tissue for implantation. The plunger 211 is located on one end of the plunger shaft, opposite the plunger handle 213. In one embodiment, each of the plunger 211, plunger shaft 212, and plunger handle 213 are separate pieces that can be fixedly attached to form the plunger assembly 210. However, in a further embodiment, the plunger assembly 210 is a single unitary member.

The plunger is conformably sized to fit within the bore, between the tongue blade, which is positioned along a bottom surface of the bore, and a top surface of the bore. A length of the plunger is dependent on a length of the bore, a desired depth for implanting, and a length of the plunger shaft. The plunger shaft 212 is a straight member that is sized to fit within the bore, next to the tongue blade shaft. The plunger shaft can have a circular or non-circular shape. A length of the plunger shaft 212 can be dependent on a length of the incising body, as well as a desired depth of implantation. The width of the plunger shaft is based on the size of the bore and the size of the tongue blade shaft. In one embodiment, a width of the plunger is greater than the width of the plunger shaft and the plunger is affixed to the plunger shaft to form an L-shape.

The plunger handle 213 can be perpendicularly affixed to the plunger shaft 212 opposite the plunger 211, so that the proximal end of the plunger shaft is perpendicularly affixed to a portion of the plunger to form an L-shape. The L formed by the plunger handle and the plunger can face the same or opposite direction.

The side-by-side two-part plunger can be made from surgical grade stainless steel, a durable plastic, such as Polyetheretherketone, rubber, or related materials, as well as from a combination of materials. In one embodiment, the tongue blade is formed from stainless steel, while the tongue blade shaft and tongue blade handle are formed from durable plastic. Alternatively, the plunger is formed from rubber, while the plunger shaft and plunger handle are formed from durable plastic. Other materials are possible.

Referring back to FIG. 25, the side-by-side two-part plunger is assembled inside the incising body. The tongue blade is positioned along a bottom surface of the bore, while the tongue blade shaft is partially located within the bore and the tongue blade handle is located outside of the incising body. The plunger assembly is positioned to cooperatively operate with the tongue blade assembly to clear a pathway or cavity in the tissue and insert the implant into the cavity. The plunger shaft is partially positioned within the bore along side the tongue blade shaft and the plunger is positioned above the tongue blade. During deployment of the tongue blade assembly, the tongue blade handle is pushed distally into the incising shaft, which urges the tongue blade through the tip of the incising shaft and into the tissue.

To deploy the plunger assembly, the plunger handle is pushed distally into the incising shaft, which pushes the implant through the bore and into the cavity formed in the tissue by the tongue blade. Once the implant is positioned, the tongue blade assembly and the plunger assembly are retracted backwards so that the tongue blade and the plunger are moved into the incising body of the implantation instrument, which is thereafter removed.

Use of the implantation instrument with the two-part plunger facilitates maintenance of a sterile environment during implant. FIG. 28A is a diagrammatic view illustrating the opening into a subcutaneous site. An incision site is located on the external layer of skin 221 of a patient. The incision site 227 is prepared for insertion of the implantation instrument 220 by applying lidocaine or other drugs, including anesthetic and antiarrhythmic drugs to the skin. Prior to implantation, the tongue blade assembly 225 and the plunger assembly 226 are fully retracted, so that the tongue blade and the plunger are fully located within the bore. In one embodiment, the implant 228 is inserted into the bore of the incising body 224, and positioned above a top surface of the tongue blade and adjacent to the plunger. In a further embodiment, the implantation instrument 220 is prepackaged with the implant 228.

To make the incision, the implantation instrument 220 is positioned at an angle at the incision site, so that that the sharp cutting edge of the incising body contacts the skin 221. A downward force is applied to at least one of the tongue blade handle, plunger handle, and incising body, which urges the sharp cutting edge to dissect through the skin 221 at the incision site 227 and to enter into the subcutaneous fat layer 222. The subcutaneous fat layer 222 is located below the skin 221 and above the muscle 223.

Figure 28B:
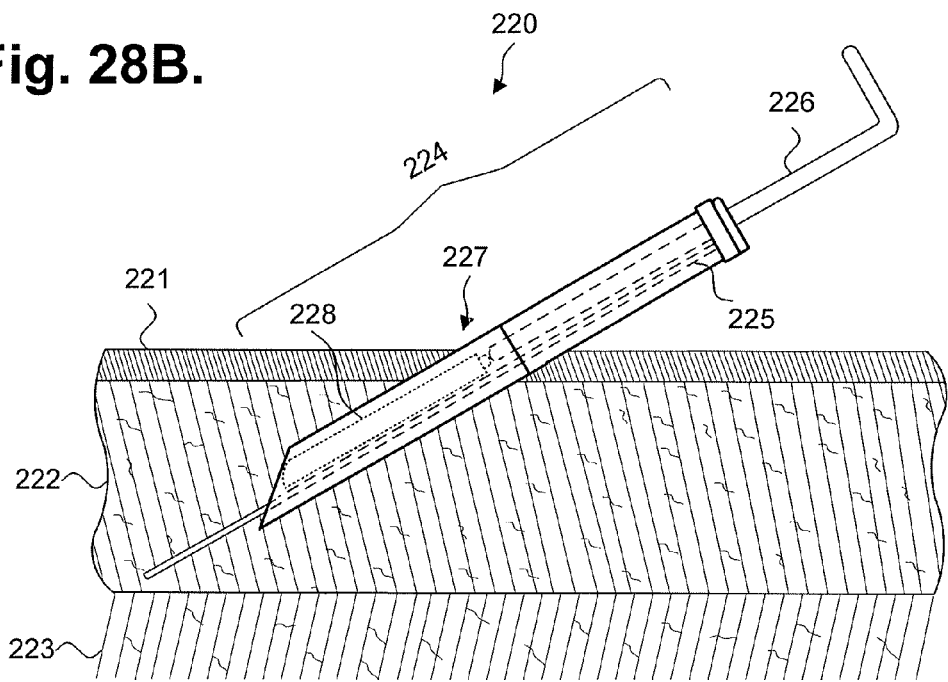
FIG. 28B is a diagrammatic view illustrating the clearing of a subcutaneous site using a tongue blade assembly in accordance with a further embodiment.

Once the implantation instrument 220 is inserted, the tongue blade assembly and the plunger assembly can be separately deployed to place the implant. FIG. 28B is a diagrammatic view illustrating the clearing of a subcutaneous site using a tongue blade assembly 225 in accordance with a further embodiment. The tongue blade assembly 225 is deployed downward into the tissue by applying distal force to the tongue blade handle, which slides the tongue blade assembly through the incising body and out of the bore opening beyond the tip of the incising shaft. The tongue blade assembly 225 is deployed until the tongue blade handle contacts the circular collar. During deployment, the tongue blade gradually exits the bore of the incising body 224 and enters the subcutaneous fat layer 222 to clear or "tunnel" a pathway or cavity for the implant 228 using the sharp cutting edge formed around a periphery of the tongue blade.

Figure 28C:
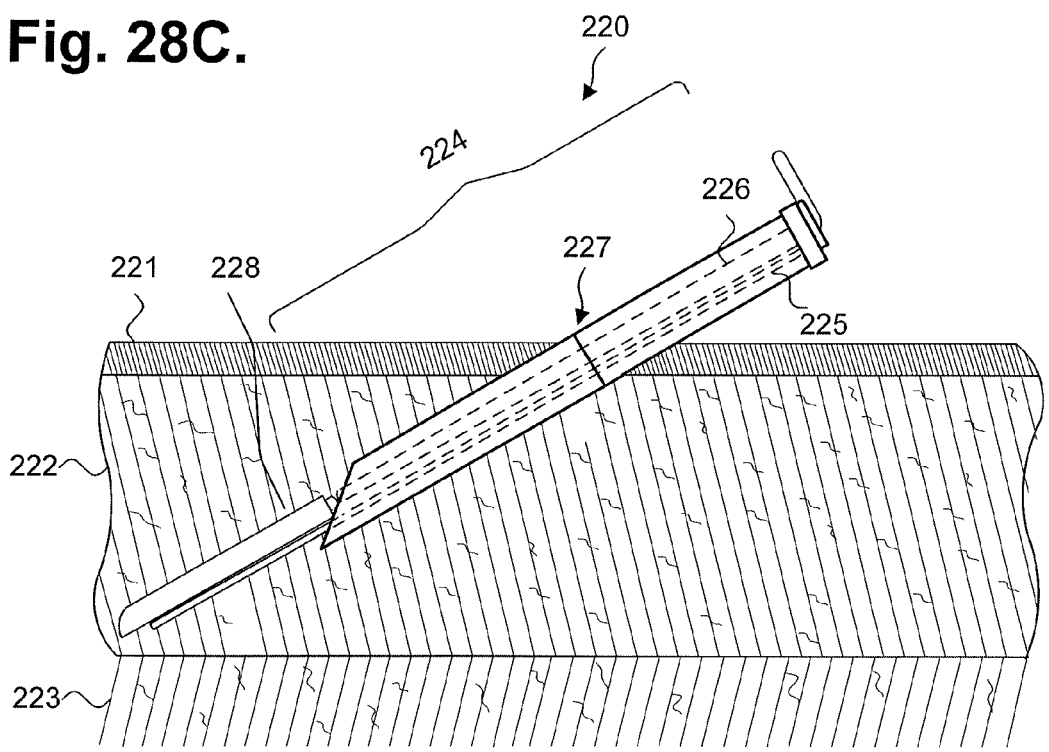
FIG. 28C is a diagrammatic view illustrating the subcutaneous implantation of an object using a plunger assembly in accordance with a further embodiment.

After the cavity is cleared, the implant 228 can be inserted into the cavity in the subcutaneous fat 222 layer using the plunger assembly. FIG. 28C is a diagrammatic view illustrating the subcutaneous implantation of an object in accordance with a further embodiment. The plunger assembly 226 is deployed by applying a downward force on the plunger handle, which slides a portion of the plunger shaft and the plunger through the bore of the incising body 224. The plunger eventually contacts the implant 228 and pushes the implant through the bore opening into the cavity formed in the subcutaneous fat layer 222 by the tongue blade. In one embodiment, the tongue blade is deployed in the tissue and the implant travels along the top surface of the tongue blade. In a further embodiment, the tongue blade is previously deployed and the implant is pushed into the cleared cavity formed by the deployed tongue blade.

Subsequent to implantation, the tongue blade assembly and the plunger assembly can be retracted simultaneously or one-at-a-time and in any order. Once retracted, the implantation instrument 220 can be removed from the patient.

FIGS. 5A-D are transverse cross-sectional views of the implantation instrument 10 illustrating, by way of example, various bore configurations. FIG. 5A illustrates an incising shaft 35 with a substantially rectangular bore 36. FIG. 5B illustrates an incising shaft 37 with a substantially square bore 38. FIG. 5C illustrates an incising shaft 39 with a substantially oval bore 40. And FIG. 5D illustrates an incising shaft 41 with a substantially hexagonal bore 42. Note the circumferential shape of the incising shaft need not follow the internal shape of the incising shaft bore. Other bore configurations, including variations on oval, rectangular, square, pentagonal, hexagonal, heptagonal, octagonal, and similar equilateral or non-equilateral shapes, are feasible.

In the described embodiment, the rectangular bore 36 has the dimensions of approximately 10 mm by 5 mm. The syringe body bore 23 has a length of approximately 5 cm.

FIG. 6 is a segmented side view of a clearing trocar 45. The clearing trocar 45 consists of a beveled tip 47 on the distal end of the clearing trocar 45 and a clearing trocar shaft 46 affixed, either fixably or removably, to the distal end of a plunger 16.

During a clearing operation, the clearing trocar 45 is fully extended from the distal bore opening 14 of the incising shaft 11. The clearing trocar shaft 46 is only long enough to clear out the subcutaneous site. The plunger 16 acts as a stop that limits the extent of penetration of the clearing trocar 45, thereby preventing the clearing trocar 29 from incising too deeply into the subcutaneous fat 29. In addition, the clearing trocar 29 is sized to approximate the girth of the incising shaft bore 22 and will clear a subcutaneous site only as wide as minimally necessary to facilitate implantation of the implantable object. In the described embodiment, the clearing trocar 45 has a length of approximately 2 cm beyond the tip of the syringe body 15.

FIG. 7 is a segmented side view of a pushing stylet 50. The pushing stylet 50 consists of a blunt tip 52 on the distal end of the pushing stylet 50 and a pushing stylet shaft 51 affixed, either fixably or removably, to the distal end of a plunger 16.

During a delivery operation, the pushing stylet 50 is extended from the distal bore opening 14 of the incising shaft 11. The pushing stylet shaft 51 is only long enough to clear the distal bore opening 14. The plunger 16 acts as a stop that limits the lateral travel of the pushing stylet 50. In the described embodiment, the pushing stylet 50 has an additional length of approximately 2 cm beyond the tip of the syringe body 15.

Figure 8A:
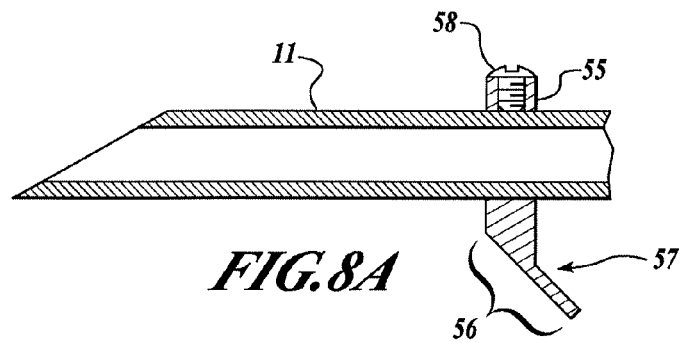
FIGS. 8A-8B are section views illustrating penetration limiting mechanisms for use with the implantation instrument.
Figure 8B:
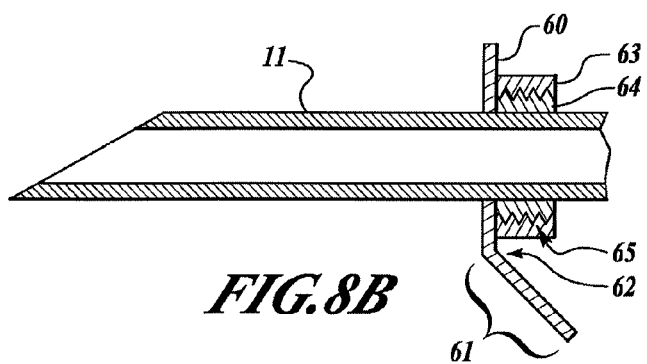

FIGS. 8A-8B are section views illustrating penetration limiting mechanisms for use with the implantation instrument 10. The penetration limiting mechanisms limit the depth of penetration of the incising shaft 11 and help prevent excessive penetration. FIG. 8A shows a fixed penetration limiting mechanism consisting of a stopping flange 55 attached to the incising shaft 11. The position of the stopping flange 55 along the incising shaft 11 can be adjusted by loosening a hold-down screw 58 and sliding the stopping flange 55 into the desired location. The lower edge of the stopping flange 55 has a bend 57 with an angle T, preferably between approximately 30° and 60°, thereby forming an elbow 56 which stops lateral travel upon contact with the skin.

FIG. 8B shows an adjustable penetration limiting mechanism consisting of a stopping flange 60 attached a frictional collar 64. The stopping flange 60 and frictional collar 64 are slidably attached to the incising shaft 11. An adjustable collar 64, preferably in threaded communication 65 with the frictional collar 64, manually stops deployment of the penetration limiting mechanism by tightening the frictional collar 64 against the incising shaft 11. The lower edge of the stopping flange 60 has a bend 62 with an angle D, preferably between approximately 30° and 60°, thereby forming an elbow 61 which stops lateral travel upon contact with the skin.

Figure 9:
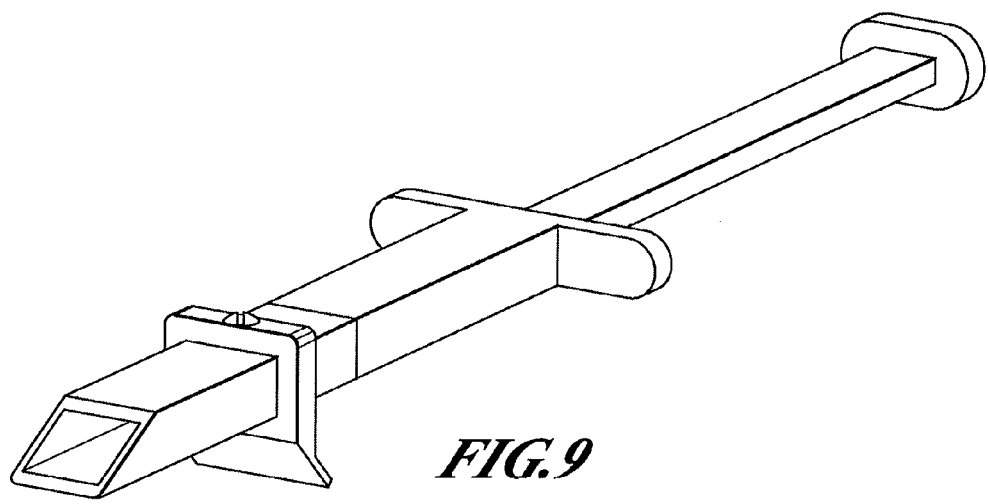
FIG. 9 is a perspective view of an instrument for implanting objects in a subcutaneous or other tissue location in accordance with a further embodiment of the present invention.

FIG. 9 is a perspective view of an instrument for implanting objects in a subcutaneous or other tissue location in accordance with a further embodiment of the present invention. The instrument is equipped with the stopping flange 55 shown in FIG. 8A. Other forms of penetration limiting mechanisms, both fixed and adjustable, could be used, as would be readily apparent to one skilled in the art.

In addition to being flat and chisel-like, the cutting edge of the incising shaft can be shaped as a progressive cutting or clearing blade, or a dissecting tool suitable for use in facilitating subcutaneous insertion. FIGS. 10A-10C are perspective views of progressive cutting edges 71, 81, 91 formed on distal edges of incising shafts 70, 80, 90 in accordance with further embodiments. The cutting edge can be shaped to facilitate subcutaneous insertion, such as when necessary to penetrate areas of thick epidermis, for instance, on the hands or feet, or animal hide. For instance, the cutting edge 71 can be shaped into a point or semi-point, which can initially pierce and progressively enlarge an implantation site. Similarly, the cutting edge 81 can be shaped into a rounded or curved edge, which can also progressively enlarge an implantation site, but without initial piercing. In addition, the cutting edge 91 upwardly curved or angled, which can help shape the implantation site to more closely follow the contours of the object to be implanted. Other cutting edge shapes are possible. Moreover, dissecting tools could be used in addition to or in lieu of the progressive cutting edges, such as a flat or shaped dissecting tool.

The pointed cutting edge is narrow at the tip and gradually extends outward to form a wider cutting surface. The narrow tip is first introduced to the patient's dermis to prevent tearing, gouging, or similar injury that can be caused by a flat wide surface. An incision formed by the narrow tip is gradually increased in size as the cutting edge of the implantation instrument is pushed further into the patient. To further prevent damage to the tissue of a patient, a safety stop, safety door, and captive incising body can also be added to the implantation instrument. Together, the pointed cutting edge, safety stop, safety door, and captive incising body provide implantation of a medical device with convenient use, minimal tissue damage, and reduced exposure to the inside of the incising body and medical device.

Figure 29:
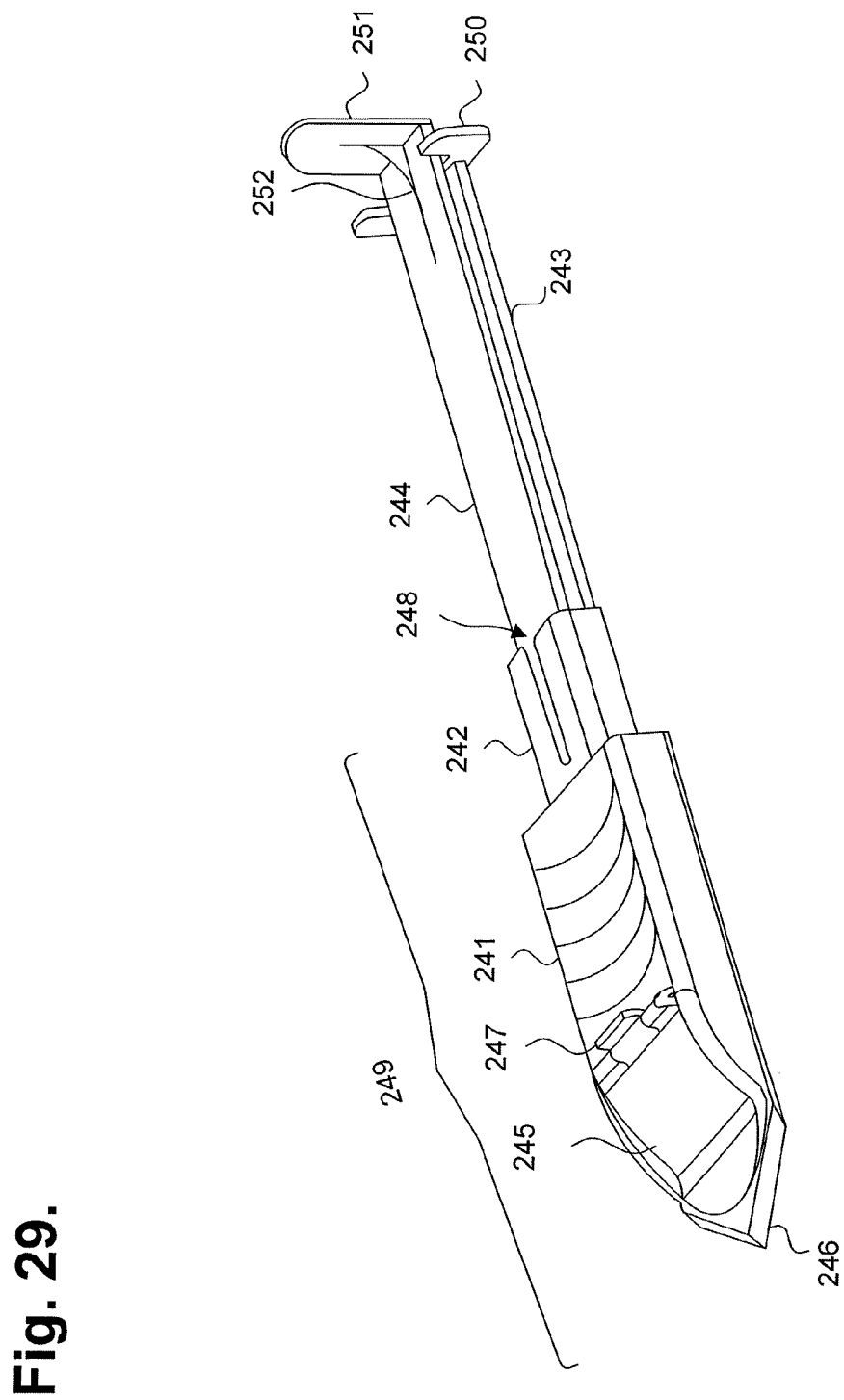
FIG. 29 is a perspective view of an implantation instrument with a two-part plunger in accordance with a further embodiment.

The captive incising body reduces the risk of infection by preventing removal of the tongue blade assembly and the plunger assembly. FIG. 29 is a perspective view of an implantation instrument 240 with a two-part plunger in accordance with a further embodiment. The implantation instrument includes an incising body 249 and a two-part plunger. The incising body 249 is formed by an incising shaft 241, which is fixedly attached on one end to a syringe body 242. A hollow non-circular cavity is formed within the incising shaft 241, which extends to a cavity opening (not shown) proximate to the pointed cutting edge 246. The cavity is sized to receive and house an implant for implanting in a patient. The syringe body includes a coaxial non-circular hollow bore, which can have the same height as the cavity, but a shorter width. In a further embodiment, the cavity and the bore are non-circular. The incising shaft and the syringe body are positioned end-to-end, so that one end of the syringe body is centered on an end of the incising shaft to align a portion of the cavity of the incising shaft with the bore of the syringe body. An opening extends from one end of the incising body continuously through an opposite end on the syringe body. In one embodiment, the dimensions of the incising shaft 241 are approximately 13 mm×25 mm×40 mm, while the dimensions of the syringe body 242 are approximately 13 nm×28 nm×24 nm. In a further embodiment, the height of the syringe body 242 can also be shorter than the height of the incising shaft 241.

A pointed cutting edge 246 is formed on an end of the incising shaft 241, opposite the syringe body to prevent coring of skin and flesh when used to implant a medical device or other materials. The pointed cutting edge 246 tapers around an outer surface to form a sharp beveled cutting blade on a bottom end of the incising shaft, which can form an incision in the patient's skin. Other shapes of the cutting edge are possible.

The incising body 249 houses a portion of the two-part plunger, which includes a tongue blade assembly 243 and a plunger assembly 244. The tongue blade assembly clears a pathway in the tissue for inserting the implant and can include a tongue blade (not shown), a tongue blade shaft, and a tongue blade handle 250. The tongue blade is located on one end of the tongue blade shaft, opposite the tongue blade handle 250. In one embodiment, each of the tongue blade, tongue blade shaft, and tongue blade handle are separate pieces that are fixedly attached. In a further embodiment, the tongue blade assembly is unitarily formed. The tongue blade assembly is further discussed below in detail with reference to FIG. 30. The plunger assembly urges the implant out of the incising body and into a cavity formed in the tissue for implantation. The plunger assembly includes a plunger (not shown), a plunger shaft 244, and a plunger handle 251. The plunger is located on one end of the plunger shaft, opposite the plunger handle. In one embodiment, each of the plunger, plunger shaft, and plunger handle are separate pieces that are fixedly attached. In a further embodiment, the plunger assembly is unitarily formed. The tongue blade assembly and the plunger assembly are further discussed below with reference to FIG. 30.

The cover 245 is positioned over the cavity opening on the incising shaft and redefines the front profile of the implantation instrument to aid in implantation of an implantation device, while reducing trauma to tissue adjacent to the implantation site. Specifically, the cover 245 is affixed to a top surface of the incising shaft 241 at the cavity opening, opposite the syringe body, via an attachment assembly, including a hinge, pins, screws, adhesive, or other attachment means. The cover 245 prevents coring of surrounding tissue when the implantation device is inserted into the patient. Additionally, during insertion of the instrument, the cover 245 can reduce or prevent bruising or tearing of skin that can be caused by the top surface of the end of the incising body by the cutting edge by guiding tissue over the end during implantation. The cover is further discussed below with reference to FIGS. 30 and 31A-C.

A safety stop 247 can also be affixed to the top surface of the incising shaft on a distal end. The safety stop 247 extends away from the incising shaft to form a wall that prevents insertion of the implantation instrument into a patient at a particular point upon contacting a surface of the patient's skin. The safety stop 247 can be formed as part of the cover attachment mechanism or separate from the cover attachment mechanism. The safety stop is further discussed below with reference to FIG. 30.

The implantation instrument with a pointed cutting edge, safety stop, safety door, and captive incising body can be designed for disposable single use or for reuse. The disposable implantation instrument can be assembled and prepackaged for purchase, while reusable implantation instrument can be purchased as a unitary instrument or as separate parts. FIG. 30 is an exploded perspective view 260 of the instrument for implanting sensors or solid materials in a subcutaneous or other tissue location shown in FIG. 29. As described above with reference to FIG. 29, the incising body of the implantation device is formed from the incising shaft 261 and the syringe body 262. The incising body 261 can be formed from an inverted U-shape member 261, which has a cutout 276 on a top surface from which the sides of the U-shape member are tapered downward to form a concave opening. The U-shape member is fixedly attached to a bottom surface 269 through frictional, adhesive, or preformed constructive means. The bottom surface 269 is a thin flat surface that can be attached on one end to a pointed cutting surface 268. Specifically, the cutting surface 268 is affixed to the bottom surface at the point at which the ends of the tapered U-shape member 261 sides are positioned on the bottom surface. In a further embodiment, the incising shaft is unitarily constructed. Together, the U-shape member 261 and the bottom surface 269 form a cavity within which the implant can be located. The cavity can extend through a cavity opening on the end of the incising body at which the pointed cutting surface is located. In one embodiment, both the incising shaft bottom surface 269 and pointed cutting edge 268 are made from surgical grade stainless steel, while the U-shaped member is made from a durable biocompatible plastic, such as Polyetheretherketone, or related materials. In a further embodiment, only the pointed cutting edge 268 is made from surgical grade stainless steel, while the remaining parts of the incising shaft are made from the durable biocompatible plastic. Additionally, indented grooves or extended guides 279 can be formed on a top surface of the incising shaft to assist a physician or other administering agent to grip the implantation device during insertion into the patient.

Similarly, the syringe body can be formed from an inverted U-shape member 262, which is generally shorter and narrower than the incising shaft. The syringe body U-shape member 262 is fixedly attached to a flat bottom surface 270 that has the same length and width dimensions as the syringe body U-shape member. The syringe body U-shape member 262 and flat bottom surface 270 can be affixed through frictional, adhesive, or preformed constructive means. In a further embodiment, the syringe body can be unitarily constructed. Together, the syringe body U-shape member 262 and the flat bottom surface 270 form a hollow bore 297. The bore 297 can be used to guide the tongue blade shaft and plunger shaft during implantation. The syringe body can be constructed from stainless steel, biocompatible plastic, or other related materials. In one embodiment, the bottom surface of the syringe body is made from stainless steel, while the syringe body U-shape member is made from durable biocompatible plastic. Other materials are possible.

Once the incising shaft and the syringe body are formed, one end of the incising shaft, opposite the pointed cutting edge, is affixed to the syringe body through frictional, adhesive, or preformed constructive means. Specifically, the syringe body is centered on the incising shaft, so that the bore is aligned with a portion of the cavity to form a continuous hollow opening in the incising body. The opening holds and guides portions of the two-part plunger, which includes a tongue blade assembly and a plunger assembly.

The tongue blade assembly includes a tongue blade 265, a tongue blade shaft 266, and a tongue blade handle 267. The tongue blade 265 is formed as a thin flat surface with a rounded edge on one side and a straight edge on the other side that is sized to conformably fit the width of the incising shaft. A top surface of the rounded edge can taper to form a sharp beveled cutting edge 272 around a periphery of the tongue blade 265. The sharp beveled cutting edge can clear a pathway in the tissue of a patient to guide placement of the implant.

The straight edge of the tongue blade is affixed to one end of the tongue blade shaft 266, opposite the tongue blade handle 267, which is affixed on the other end of the tongue blade shaft. The tongue blade shaft 266 is a flat thin member that facilitates deployment of the tongue blade into the tissue to clear or "tunnel" a pathway or cavity for implanting. A width of the tongue blade shaft 266 is smaller than the width of the tongue blade and the tongue blade shaft is centered on the straight edge of the tongue blade. Also, a length of the tongue blade shaft 266 is dependent on the hollow opening formed by the cavity and the bore, desired incision depth, size of the implant, and size of the tongue blade. The tongue blade handle 267 facilitates movement of the tongue blade assembly and can be constructed to form an H-shaped member having a top cutout 277 and a bottom cutout 278. The bottom cutout 278 is sized to receive the tongue blade shaft, which is fixedly attached. The top cutout 277 is sized to receive the plunger shaft 266, which slides back and forth within the tongue blade handle during deployment and retraction of the plunger assembly.

The plunger assembly includes a straight flat plunger shaft 263 with a rounded plunger edge 273, plunger shaft 263, and plunger handle 264. The plunger assembly contacts and pushes the implant through the incising shaft cavity and out the cavity opening. The plunger 273 is a rounded edge that is formed on one end of the plunger shaft 263. The rounded edge of the plunger contacts the implant for pushing through the cavity and out of the cavity opening. In one embodiment, a containment edge (not shown) can be formed around a periphery of the rounded plunger end to prevent removal of the plunger assembly from the incising body. In a further embodiment, the plunger 273 is a separate piece that can be fixedly attached to the plunger shaft 263. The plunger shaft is a straight member that moves the plunger back and forth in the cavity. A plunger handle 264 is perpendicularly affixed to the end of the plunger shaft 263 opposite the rounded plunger 273. The plunger handle 264 and plunger shaft 263 can be affixed through frictional, adhesive, or preformed constructive means.

Portions of, or the entirety of, the tongue blade assembly and the plunger assembly can be made from surgical grade stainless steel, a durable biocompatible plastic, such as Polyetheretherketone, or related materials, as well as from a combination of materials. In one embodiment, the tongue blade is formed from stainless steel, while the tongue blade shaft and tongue blade handle are formed from durable biocompatible plastic. In a further embodiment, the plunger assembly is made entirely of biocompatible plastic.

Once formed, the incising shaft can be constructed around the tongue blade and rounded plunger edge, while the syringe body is constructed around the tongue blade shaft and the plunger shaft. However, if the incising shaft and syringe body are preconstructed, the tongue blade shaft affixed to the tongue blade and the plunger shaft with the rounded plunger edge can be distally inserted through the cavity opening of the incising shaft and proximally guided into the syringe body. The syringe body can be previously affixed to the incising shaft or can be affixed subsequent to insertion of the tongue blade assembly and plunger assembly. Once positioned in the hollow opening, the tongue blade handle is affixed to the tongue blade shaft and the plunger handle is affixed to the plunger shaft.

The cover 271 is attached to, or otherwise extends from the top of the incising shaft at the edge of the cutout 276 downwards towards a the pointed cutting surface 268 and covers the cavity opening. The cover 271 attaches to the top surface of the incising shaft U-shape member 261 at an attachment point via an attachment assembly 274. In one embodiment, the attachment assembly consists of a hinge, pins, screws, adhesive, or other attachment means. In a further embodiment, the cover 271 is unitarily constructed as an extension of the top surface of the incising shaft U-shape member 261. A crease or indentation in the top of the incising shaft U-shape member 261, adjacent to the cover 271, allows the cover 271 to pivot away from the cavity opening. Other attachment assemblies are possible.

The cover 271 rests in a closed position unless forced opened by applying a pushing force against the bottom surface of the cover 271. In the closed position, the cover 271 conceals the cavity opening. When opening, the cover 271 can be pivoted away from the incising shaft revealing the cavity opening. For example, during implantation, the cover 271 can be urged open through applied pressure to the tongue blade 265 through the tongue blade shaft 266 or the implant, as further described below with reference to FIGS. 31A-C.

The dimensions of the cover 271, at a minimum, extend beyond the inner perimeter of the cutout 276 in the incising shaft to conceal the entire cavity opening and, preferably, are equal to the outer perimeter. A cover 271 that is larger than the distal cavity opening utilizes the outer surface of the incising body as support to prevent the cover 271 from moving, or being pushed, inward into the cavity opening under force of the surrounding tissue during implantation. The dermis and other tissue along the implantation axis are instead guided over the cover 271 during dissection and implantation, as further described below with reference to FIGS. 31A-C.

A stop 275, or other penetration limiting mechanism, extends from a top surface of the incising shaft U-shape member, adjacent to the hinge assembly 274. In a further embodiment the stop 275 is constructed as part of the hinge assembly 274. The stop 275 limits the depth of penetration of the incising body to the upper end of the cover 271 at the attachment point, as further described below with reference to FIGS. 31A-C.

Figure 31A:
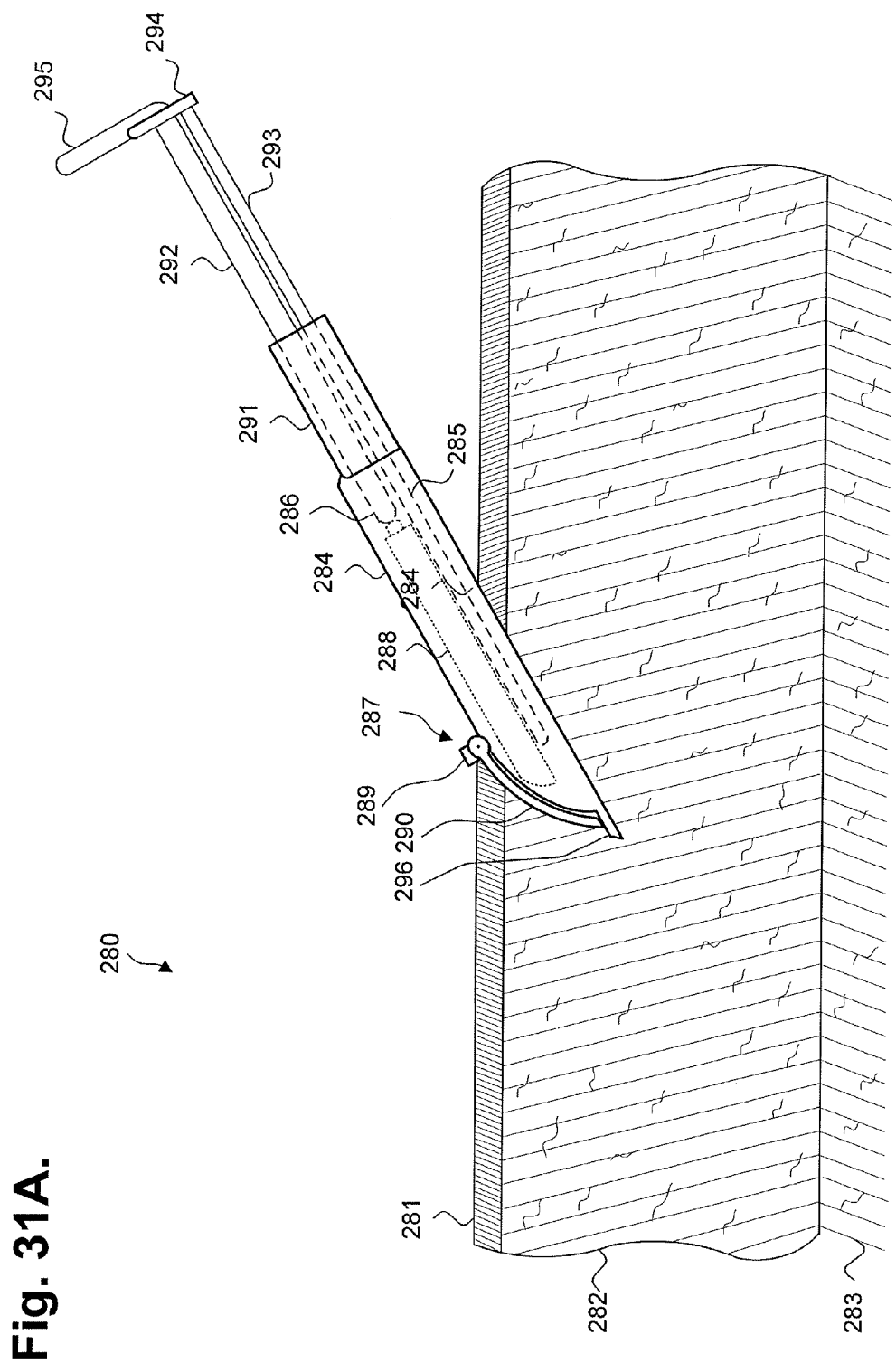
FIG. 31A is a diagrammatic view illustrating the dissecting a subcutaneous site in accordance with a further embodiment.

The implantation instrument with a pointed cutting edge, safety stop, safety door, and captive incising body provides a safe and sterile environment for implanting a medical device, while ensuring convenient and efficient use. FIG. 31A is a diagrammatic view 280 illustrating the opening into a subcutaneous site in accordance with a further embodiment. An incision site 287 is located on the external layer of skin 281 of a patient and prepared for insertion of the implantation instrument by applying lidocaine or other drugs, including anesthetic and antiarrhythmic drugs to the skin. An implant 288 is inserted into the incising shaft 284 cavity of the implantation instrument or alternatively, the implant 288 is prepackaged in the cavity. Specifically, the implant 288 is positioned within the cavity above a top surface of the tongue blade 285 and adjacent to the plunger 286. Prior to implantation, the tongue blade assembly and the plunger assembly are fully retracted and the cover 290 is in a closed position. The straight edge of the tongue blade 285 rests against an inner surface of the syringe body 291 closest to the tongue blade handle 294. Additionally, a distal tip of the plunger, opposite the plunger shaft, rests against the inner surface of the syringe body, above the tongue blade 285. In this embodiment, the tongue blade 285 and the plunger 286 are captively held in the incising shaft 284 to prevent removal of the tongue blade and plunger for maintaining a sterile environment.

The implantation instrument is positioned at an angle at the incision site with a bottom surface of the sharp cutting edge contacting the skin 281. When a downward pressure is applied to the implantation instrument, the sharp cutting edge pierces the skin 281 at the incision site 287 to enter the subcutaneous fat layer 282, which is located below the skin 281 and above the muscle 283. The implantation device is urged into the tissue at the incision site beyond the tip of the incising shaft until the safety stop 289 contacts a top surface of the skin 281. During insertion of the implantation instrument, the cover 290 remains in a closed position to prevent coring of the subcutaneous fat layer. The surface of the skin slides over the concave cover as the implantation instrument is inserted in the patient.

Figure 31B:
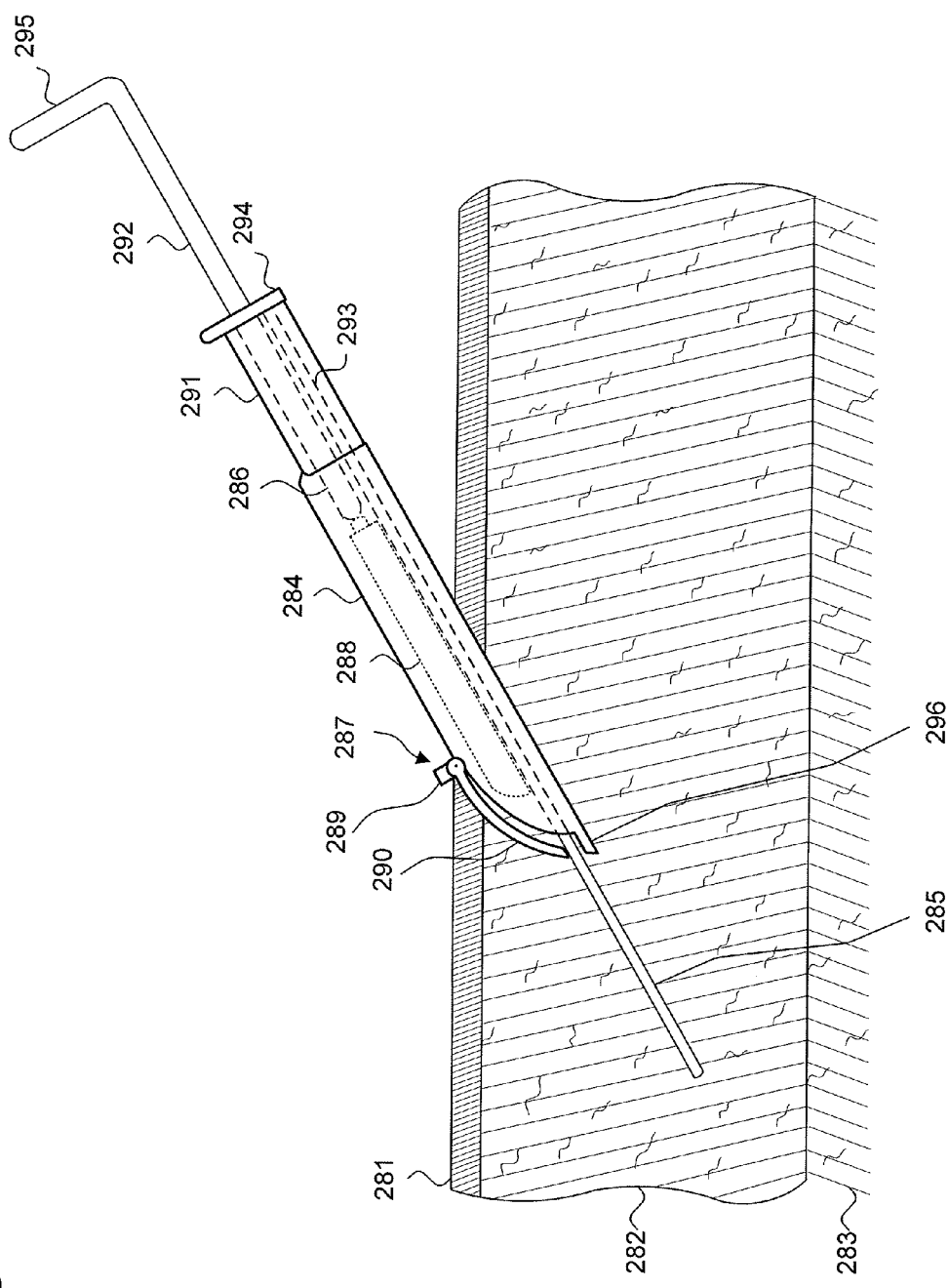
FIG. 31B is a diagrammatic view illustrating the clearing of a subcutaneous site using a tongue blade assembly in accordance with a further embodiment.
Figure 31C:
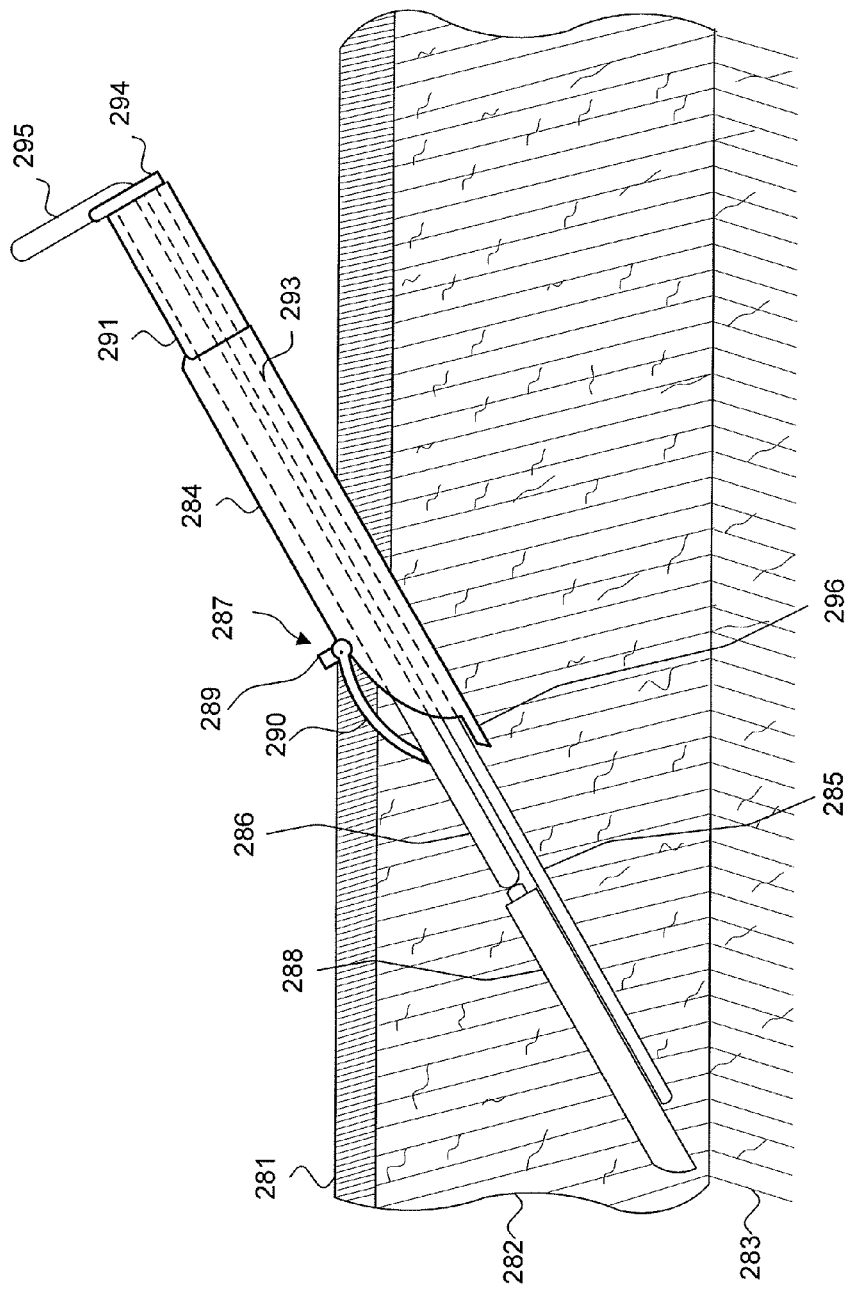
FIG. 31C is a diagrammatic view illustrating the subcutaneous implantation of an object using a plunger assembly in accordance with a further embodiment.

Once the implantation instrument is inserted, the tongue blade assembly and the plunger assembly can be separately deployed. FIG. 31B is a diagrammatic view illustrating the clearing of a subcutaneous site using a tongue blade assembly in accordance with a further embodiment. The tongue blade assembly is deployed by applying distal force to the tongue blade handle 294, which slides the tongue blade 285 through the incising shaft 284 and out of the cavity via the tongue blade shaft 293. When deployed downward, the tongue blade applies force to an inner bottom surface of the cover 290, which begins to open upward to allow the tongue blade 285 to move outside of the cavity. The tongue blade assembly is deployed until the tongue blade handle 294 contacts the syringe body 291. During deployment, the tongue blade gradually exits the bore of the incising body and enters the subcutaneous fat layer 282 to clear a pathway or cavity beyond the tip of the incising shaft for the implant 288.

After the pathway or cavity is cleared, the implant can be inserted into the cavity formed in the subcutaneous fat layer using the plunger assembly. FIG. 30C is a diagrammatic view illustrating the subcutaneous implantation of an implant 288 using a plunger assembly in accordance with a further embodiment. The plunger assembly is deployed by applying distal force to the plunger handle 295, which slides the plunger 286 through the cavity of the incising shaft 284. Eventually, the plunger contacts the implant 288 and pushes the implant 288 through the cavity opening into the cavity formed in the subcutaneous fat layer 282 along the pathway formed by the tongue blade 285. Movement through the bore opening causes the implant 288 to contact the cover 290 and force the cover to further open to allow passage of the implant 288 from the cavity. More specifically, the implant 288 contacts an inner surface of the cover, which forces the cover to move upwards and away from the pointed cutting edge 296 to provide access to the cavity in the subcutaneous fat layer 282. The plunger 286 pushes the implant 288 out of the cavity opening for accurate placement in the tissue 282.

Subsequent to implantation of the implant 288, the tongue blade assembly and the plunger assembly can be retracted simultaneously or one-at-a-time. If the plunger assembly is retracted first, the cover 290 moves downward, toward the cutting edge 296, as the plunger 286 moves completely within the cavity of the incising body, to rest on a top surface of the tongue blade 285. Thereafter, the tongue blade assembly is retracted by sliding the tongue blade 285 completely within the cavity of the incising shaft. The cover 290 continues to move downward toward the cutting edge 296 until the cover 290 contacts a bottom surface of the incising shaft 284 and a closed position is reached.

The tongue blade assembly is retracted until the straight edge of the tongue blade contacts the inner surface of the incising shaft 284 at the point of affixation to the syringe body 291. The plunger assembly is retracted until the containment edge of the plunger also contacts an inner surface of the incising body at the affixation point. Accordingly, in one embodiment, the tongue blade assembly and the plunger assembly are contained within the implantation instrument. In a further embodiment, each of the tongue blade assembly and plunger assembly can be removed from the implantation instrument. Once retracted, the implantation instrument can be removed from the patient.

FIG. 11 is a longitudinal cross-sectional view of a subcutaneous implantation instrument 100 in accordance with a further embodiment. A dissecting tool assembly 101 is removably affixed to the distal end of the incising shaft 11 with a coupling sheath 103, which can be constructed as an over sleeve frictionally fit over the incising shaft 11, a snap-off assembly that detaches from the incising shaft 11 by twisting or distal movement, or some other type of coupling that is non-integral to the incising shaft 11. The dissecting tool assembly 101 includes a needle tip 102 that defines a lumen that internally interfaces to the bore opening 14 of the incising shaft 11 and which can be used to inject a local anesthetic agent or other liquid or semi-liquid substance into the implantation site. The needle tip 102 also progressively defines a pair of cutting blades along each outward facing edge.

FIG. 12 is a top plan view of the subcutaneous implantation instrument 100 of FIG. 11. The cutting blades are oriented longitudinally and planar to the cutting edge 13 of the incising shaft 11. The cutting blades provide cutting edges 105, which gradually increase the width of the incision made when the implantation instrument 100 is inserted subcutaneously. The cutting edges 105 can be straight, concave, convex, or a combination thereof.

Figure 14:
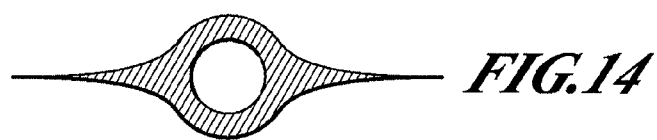
Figure 15:
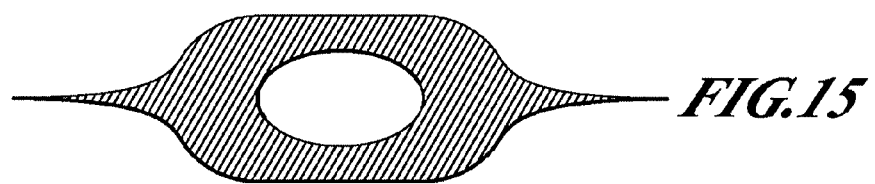

FIGS. 13-15 are transverse cross-sectional views of the dissecting tool assembly 101 of FIG. 11. On a distal end, the needle tip 102 internally defines a lumen of approximately 16 French, which tapers outwardly to a larger diameter bore and substantially non-circular bore of approximately 30 gauge on the proximal end. The cutting edges 105 become increasingly pronounced towards the proximal end of the needle tip 102. Other lumen, bore sizes, and cutting edge arrangements are possible.

Figure 16:
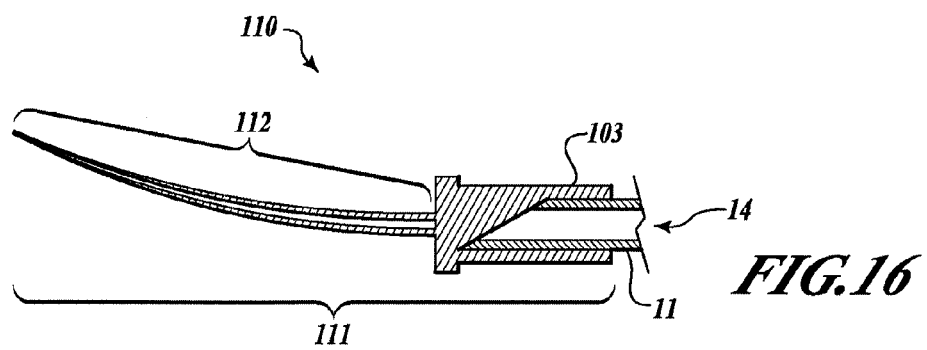
FIG. 16 is a longitudinal cross-sectional view of a subcutaneous implantation instrument in accordance with a still further embodiment.

FIG. 16 is a longitudinal cross-sectional view of a subcutaneous implantation instrument 110 in accordance with a still further embodiment. A curved dissecting tool assembly 111 bends in a gradual arc 112 upwardly towards the incising blade 11 to facilitate implantation. The curved dissecting tool assembly 111 can be used with either the straight incising shaft 11 or curved incising shaft 24. The curvature enables the implantable object to be more easily oriented parallel to the surface of the skin, rather than at an angle.

Figure 17:
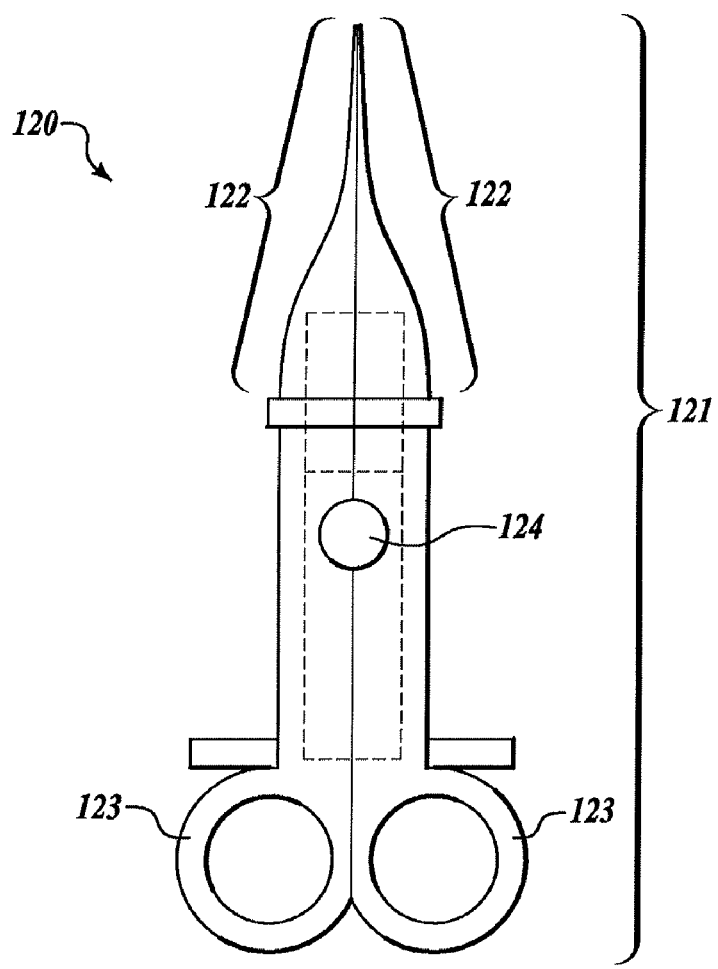
FIG. 17 is a top plan view of a subcutaneous implantation instrument in accordance with an even further embodiment.

FIG. 17 is a top plan view of a subcutaneous implantation instrument 121 in accordance with an even further embodiment. A scissored dissecting tool assembly 122 is divided into two halves, which are each attached to a handle 123 that is pivotably mounted 124, in the manner of a pair of scissors. The handles 123 can be operated outwardly to cause the distal end of the scissored dissecting tool assembly 122 to open and longitudinally cut into the surrounding tissues, thereby widening the implantation site. Once the implantation site has been suitably cleared, the scissored dissecting tool assembly 122 remains open and the plunger assembly 20 is progressive urged distally to insert the implantable object. The scissored dissecting tool assembly 122 can be straight or curved to facilitate implantation. Other forms of scissored dissecting tool assemblies are possible.

Figure 18:
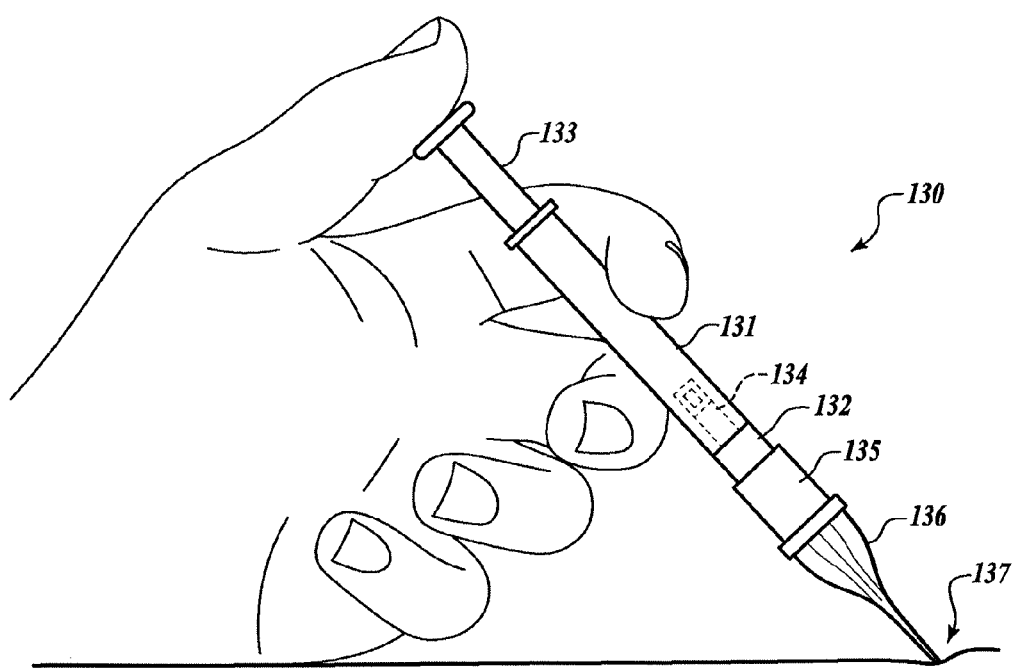
FIGS. 18-20 are perspective diagrams showing a method of use for the subcutaneous implantation instrument in accordance with one embodiment.
Figure 19:
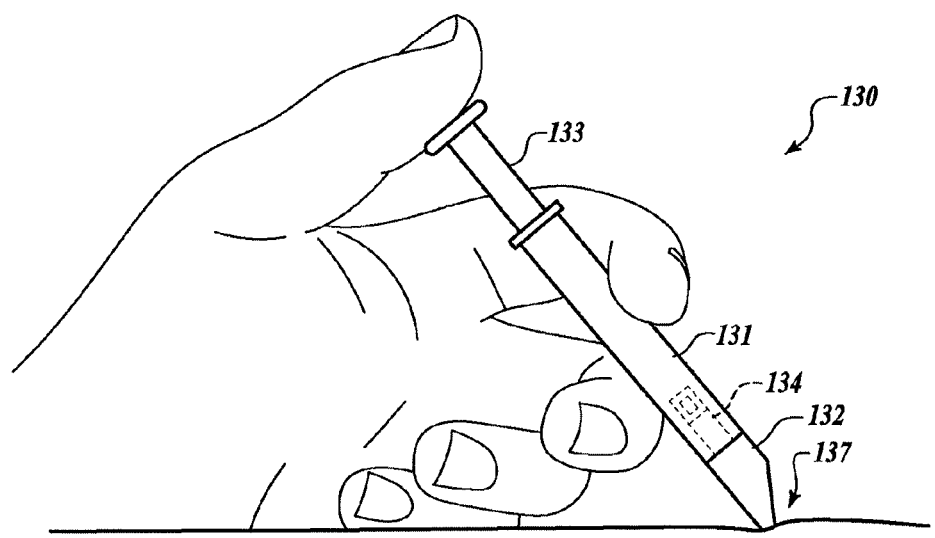
Figure 20:
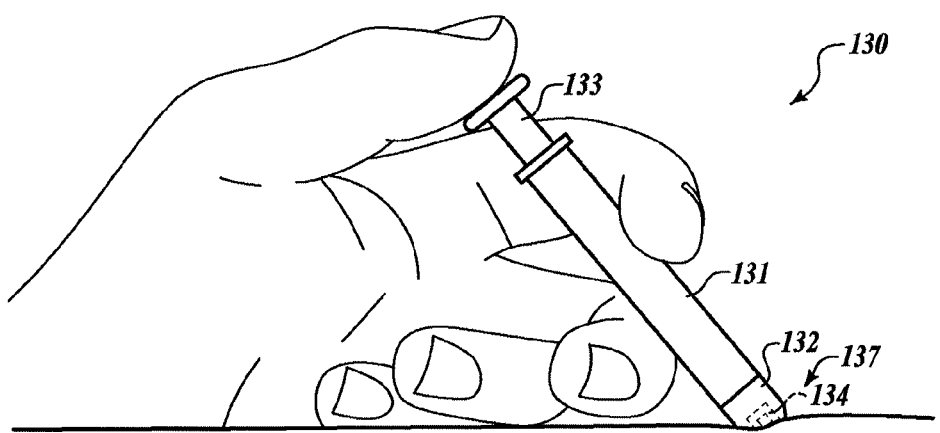

FIGS. 18-20 are perspective diagrams showing a method of use for the subcutaneous implantation instrument 121 in accordance with one embodiment. Referring first to FIG. 18, the subcutaneous implantation instrument 130 can be used for out-patient or non-surgical subcutaneous insertion of an implantable object, such as an implantable sensor, medical device, or solid material. The implantation instrument 10 enables the subcutaneous insertion of implantable objects and devices, such as sensors, without an operating room or special procedures room. The implantation instrument 10 reduces insertion of implantable objects and devices having non-conforming shapes to be the functional equivalent of an injection.

The subcutaneous implantation instrument 130 can be sold or marketed as part of a package that combines an implantable object 134 with the subcutaneous implantation instrument 130, particularly where the subcutaneous implantation instrument 130 is provided as a single-use disposable unit. Thus, the subcutaneous implantation instrument 130 can be offered with an implantable 134 object already disposed within the syringe body 131, with the entire package sealed ready for use inside sterile packaging (not shown). Alternatively, the subcutaneous implantation instrument 130 can be offered in combination with an implantable object 134 that is packaged separately.

At the outset of the procedure, an implantation site 137 can be locally anesthetized using the subcutaneous implantation instrument 130 by fitting the incising shaft 132 with a dissecting tool assembly 136, as provided in a further embodiment, described above with reference to FIG. 11 et seq. The coupling sheath 103 of the dissecting tool assembly 136 removably fits over the distal end of the incising shaft 132. The implantation site 137 is cleaned and sterilized and the needle tip 102 is inserted subcutaneously. The needle tip 102 and cutting blades on the dissecting tool assembly 136 form a progressively larger opening as the subcutaneous implantation instrument 130 is pressed downward through the skin. The plunger assembly 133 is then pressed distally to inject a local anesthetic agent into the subcutaneous implantation site.

Referring next to FIG. 19, the dissecting tool assembly 136 is withdrawn from the implantation site 137 and removed from the incising shaft 132, thereby exposing the cutting edge of the incising shaft 132. The bare incising shaft 132 is inserted into the previously cleared implantation site 137 and pressed downward. Depending upon the configuration of the cutting edges 105 of the dissecting tool assembly 136, the cutting edge of the incising shaft 132 may only need to enlarge the opening, rather than clearing a full width opening.

Referring finally to FIG. 20, downward movement of the subcutaneous implantation instrument 130 is stopped when the appropriate depth for implantation has been reached and, if necessary, is urged slight back to clear the incising shaft 137 from the actual subcutaneous implantation site. The plunger assembly 133 is again pressed distally to deploy the implantable object 134 into the incising shaft 134 and thence to insert the implantable object 134 into the subcutaneous implantation site. The incising shaft 132 is withdrawn and the wound is appropriately dressed to complete the implantation procedure. Through use of the method, the subcutaneous sensor insertion of implantable objects and devices, such as sensors, having non-conforming shapes is thereby reduced to be the functional equivalent of an injection.

While the invention has been particularly shown and described as referenced to the embodiments thereof, those skilled in the art will understand that the foregoing and other changes in form and detail may be made therein without departing from the spirit and scope of the invention.

What is claimed is:

1. A method for constructing an instrument for use in subcutaneous implantation, comprising:
    forming an incising body comprising a syringe body fixedly attached to an incising shaft and open on both distal and proximal ends;
    defining a non-circular bore along a longitudinal axis through the syringe body and the incising shaft, the bore sized to enclose an implant;
    sharpening a bottom edge of the distal end of the incising shaft;
    constructing a two-part plunger, comprising:
        constructing a tongue blade comprising a horizontal flat surface sized to fit within a width of the bore;
        sharpening a distal end of the tongue blade into a bevel;
        affixing a straight tongue blade shaft to a proximal end of the tongue blade, the tongue blade and the tongue blade shaft having a combined length exceeding a length of the bore;
        constructing a plunger comprising a horizontal flat surface and a blunt tip on a distal end of the flat surface sized to fit within a width of the bore;
        affixing a plunger shaft to a proximal end of the plunger, the plunger and the plunger shaft having a combined length exceeding the length of the bore; and
        orienting the plunger shaft side-by-side with the tongue blade shaft; and
    inserting the proximal ends of the tongue blade and the plunger of the two-part plunger through the open distal end of the bore until the distal ends of the tongue blade and the plunger are inside the bore and the proximal ends of the tongue blade and the plunger shafts extend beyond the proximal end of the syringe body of the incising body.

2. A method according to claim 1, further comprising:
    forming corresponding guide tracks on at least two of the incising body, tongue blade, and plunger.

3. A method according to claim 1, further comprising:
    affixing support shelves on an inner surface of the incising body.

4. A method according to claim 1, further comprising:
    pivotably affixing a cover on a top edge of the distal end of the incising body, the cover completely covering the open distal end of the bore in a closed position.

5. A method according to claim 1, further comprising:
    sharpening a periphery along a bottom edge of the tongue blade.

6. A method according to claim 1, further comprising:
    affixing handles on a proximal end of one or more of the tongue blade shaft and the plunger shaft.

7. A method according to claim 1, further comprising:
    inserting the implant within the bore of the incising body on top of the tongue blade and in front of the plunger.

8. A method for constructing an instrument for use in subcutaneous implantation, comprising:
    assembling an incising body, comprising:
        forming an incising shaft defining a cavity along a longitudinal axis and open on a distal end and partially open on a proximal end, the cavity sized to enclose an implant;
        forming a cutting edge on a bottom surface of the distal end of the incising shaft;
        forming a syringe body defining a bore that is shorter than the incising shaft in length and narrower than both the cavity and the incising shaft in width and height along a longitudinal axis and open on both distal and proximal ends; and
        affixing a distal end of the syringe body to a proximal end of the incising shaft with the bore aligned with the partially open proximal end of the cavity;
    assembling a two-part plunger, comprising:
        constructing a tongue blade comprising a horizontal flat surface sized to fit within a width of the cavity;
        sharpening a distal end of the flat surface of the tongue blade into a bevel;
        affixing the tongue blade to a distal end of a straight tongue blade shaft that is sized to slide longitudinally within the bore;
        constructing a plunger comprising a horizontal flat surface sized to fit within a width of the cavity, the flat surfaces of the tongue blade and plunger together sized to fit within a height of the cavity;
    affixing the plunger to a distal end of a plunger shaft that is sized to slide longitudinally within the bore, the tongue blade and plunger shafts together sized to fit within the bore; and
        orienting the plunger shaft above the tongue; blade shaft; and
    inserting proximal ends of the tongue blade and the plunger of the two-part plunger through the open distal end of the cavity until the distal ends of the tongue blade and the plunger are inside the cavity and the proximal ends of the tongue blade and the plunger shafts extend beyond the proximal end of the syringe body of the incising body.

9. A method according to claim 8, further comprising:
    forming corresponding guide tracks on at least of two of the incising body, tongue blade, and plunger.

10. A method according to claim 8, further comprising:
affixing support shelves on an inner surface of the incising body.

11. A method according to claim 8, further comprising:
pivotably affixing a cover on a top edge of the distal end of the incising body, the cover completely covering the open distal end of the cavity in a closed position.

12. A method according to claim 8, further comprising:
forming indented grooves on a top surface of the incising body.

13. A method according to claim 8, further comprising:
sharpening a periphery along a bottom edge of the tongue blade.

14. A method according to claim 8, further comprising:
affixing handles on a proximal end of one or more of the tongue blade shaft and the plunger shaft.

15. A method according to claim 8, further comprising:
inserting the implant within the bore of the incising body on top of the tongue blade and in front of the plunger.

\* \* \* \* \*